United States Patent [19]
Burtis et al.

[11] Patent Number: 5,242,803
[45] Date of Patent: Sep. 7, 1993

[54] ROTOR ASSEMBLY AND ASSAY METHOD

[75] Inventors: Carl A. Burtis, Oak Ridge; Wayne F. Johnson, Loudon; William A. Walker, Knoxville, all of Tenn.

[73] Assignee: Martin Marietta Energy Systems, Inc., Oak Ridge, Tenn.

[21] Appl. No.: 878,799

[22] Filed: May 5, 1992

Related U.S. Application Data

[60] Division of Ser. No. 359,007, May 30, 1989, Pat. No. 5,173,262, which is a continuation-in-part of Ser. No. 74,739, Jul. 17, 1987, Pat. No. 4,835,106.

[51] Int. Cl.$^5$ ............... G01N 33/53; G01N 33/543
[52] U.S. Cl. ............................ 435/7.92; 435/288; 435/291; 436/45; 436/165; 436/807; 436/518; 422/72
[58] Field of Search ............ 436/45, 165, 807, 518, 436/526; 422/72; 435/7.92, 7.94, 288, 291; 494/16

[56] References Cited

U.S. PATENT DOCUMENTS

| | | | |
|---|---|---|---|
| 3,837,217 | 3/1975 | Anderson et al. | 356/246 |
| 4,035,156 | 7/1977 | Shumate | 23/259 |
| 4,284,602 | 8/1981 | Kelton et al. | 422/72 |
| 4,314,968 | 2/1982 | Guigan | 422/64 |
| 4,412,973 | 11/1983 | Guigan | 422/72 |
| 4,469,793 | 9/1984 | Guigan | 436/45 |
| 4,470,954 | 9/1984 | Chiknas | 422/72 |
| 4,515,889 | 5/1985 | Klose et al. | 435/4 |
| 4,557,600 | 12/1985 | Klose et al. | 356/246 |
| 4,690,899 | 9/1987 | Klose et al. | 436/45 |
| 4,740,472 | 4/1988 | Burtis et al. | 436/63 |
| 4,743,558 | 5/1988 | Guigan | 436/45 |
| 4,788,154 | 11/1988 | Guigan | 436/180 |
| 4,812,411 | 3/1989 | Guigan | 435/293 |
| 4,835,106 | 5/1989 | Johnson et al. | 436/45 |
| 4,847,205 | 7/1989 | Burtis et al. | 436/45 |
| 4,883,763 | 11/1989 | Holen et al. | 436/45 |
| 4,892,708 | 1/1990 | Wogoman | 422/72 |
| 4,894,204 | 1/1990 | Cornut | 422/72 |
| 4,915,911 | 4/1990 | Klose et al. | 422/72 |
| 4,916,078 | 4/1990 | Klose et al. | 436/165 |
| 4,999,304 | 3/1991 | Robertson | 436/45 |

OTHER PUBLICATIONS

S. G. Schultz et al., "Two-Dimensional Centrifugation for Desk-Top Clinical Chemistry", *Clinical Chemistry*, vol. 31, No. 9, 1457-1463 (Sep. 1985).

C. A. Burtis et al., "Development of a Simple Device for Processing Whole-Blood Samples into Measured Aliquots of Plasma", *Clinical Chemistry*, vol. 32, No. 9, 1642-1647 (1986).

*Primary Examiner*—James C. Housel
*Assistant Examiner*—Jan M. Ludlow
*Attorney, Agent, or Firm*—Joseph A. Marasco; Harold W. Adams

[57] ABSTRACT

A rotor assembly for carrying out an assay includes a rotor body which is rotatable about an axis of rotation, and has a central chamber and first, second, third, fourth, fifth, and sixth chambers which are in communication with and radiate from the central chamber. The rotor assembly further includes a shuttle which is movable through the central chamber and insertable into any of the chambers, the shuttle including a reaction cup carrying an immobilized antigen or an antibody for transport among the chambers. A method for carrying out an assay using the rotor assembly includes moving the reaction cup among the six chambers by passing the cup through the central chamber between centrifugation steps in order to perform the steps of: separating plasma from blood cells, binding plasma antibody or antigen, washing, drying, binding enzyme conjugate, reacting with enzyme substrate and optically comparing the resulting reaction product with unreacted enzyme substrate solution. The movement of the reaction cup can be provided by attaching a magnet to the reaction cup and supplying a moving magnetic field to the rotor.

6 Claims, 28 Drawing Sheets

ROTOR ASSEMBLY AND ASSAY METHOD

The U.S. Government has rights in this invention pursuant to Contract No. DE-AC05-84OR21400 with Martin Marietta Energy Systems, Inc., awarded by the U.S. Department of Energy.

This application is a divisional application of co-pending application Ser. No. 359,007, filed May 30, 1989, now U.S. Pat. No. 5,173,262, issued on Dec. 22, 1992, which is a continuation-in-part application of co-pending patent application Ser. No. 074,739, filed Jul. 17, 1987, U.S. Pat. No. 4,835,106, issued on May 30, 1989, and entitled ROTOR FOR PROCESSING LIQUIDS USING MOVABLE CAPILLARY TUBES.

FIELD OF THE INVENTION

This invention relates generally to a rotor for processing liquids. More particularly, the invention relates to a rotor with which a number of bioanalytical processing steps can be automatically performed on a liquid and a method of using the rotor.

BACKGROUND OF THE INVENTION

Rotors for use during the processing of liquids are known. One such rotor, described in U.S. Pat. No. 3,901,658, discloses a rotor assembly for performing photometric analyses using whole blood samples. The rotor assembly includes a cell sedimentation bowl for centrifugally separating red blood cells from plasma. Following separation, the plasma is displaced from the sedimentation bowl, and measured sub-volumes are distributed to respective sample analyses cuvettes positioned in an angular array about the rotor periphery. Another rotor, described in U.S. Pat. No. 4,515,889 is utilized for mixing and incubating a sample solution with at least one reagent and optically measuring a parameter in the incubated reaction mixture. Each step of mixing, incubating and measuring is carried out under the influence of centrifugal forces generated by the rotation of the rotor. Other examples of rotors are set forth in the referenced co-pending patent application Ser. No. 074,739, filed Jul. 17, 1987, U.S. Pat. No. 4,835,106, issued on May 30, 1989, whose disclosure is incorporated herein by reference.

Historically, the aliquoting of liquid samples and diluents for use in a rotor has been performed by hand prior to introduction of the aliquot within the rotor for a processing step. It would be desirable to provide a rotor wherein a measured amount of aliquot can be automatically separated from an excess amount of liquid introduced within the rotor without the use of capillary tubes, moving parts supported within the rotor or manual intervention of an analyst.

In addition, transfer of liquids within the rotor from one chamber of the rotor to another for processing purposes has presented difficulties due to space limitations within the rotor which can be dedicated to transfer mechanisms. Hence, it would also be desirable to provide a rotor wherein liquid can be transferred from one character of the rotor to another without the use of transfer mechanisms internal of the rotor. Moreover, it would be desirable to provide a rotor having an internal passageway opening through which liquid is prevented from passing prior to the occurrence of a predetermined event, such as the insertion of a capillary tube through the passageway opening.

Conventional rotors are commonly limited in that only a limited number of processing steps can be performed within any one rotor. When analyzing a whole blood sample, for example, a large number of processing steps may be involved including a separating of plasma component of the sample from the cellular component, obtaining a measured aliquot of plasma and then mixing the aliquot with a reagent to induce a reaction which is monitored. Additional processing steps may include dilution, separation, protein removal and washing.

Other examples of an analysis method or technique involving a large number of processing steps are enzyme-linked immunosorbent assay (ELISA) and heterogeneous enzyme immunoassays which are used to detect and quantitate either antigens or antibodies in biological samples. The ELISA technique utilizes enzyme-labeled immunoreactants (antigen or antibody) covalently bound to a solid support such as the inside of test tubes, the surface of beads, or the surface of individual wells in microtiter plates. Although popular and widely used in bioanalysis, ELISA assays are difficult to completely automate since they require separation of free-labeled antigen (or antibody) from the labeled antigen (or antibody) bound to the solid support. Also, ELISA procedures require a series of sequential manipulations in order to perform an assay. For example, even a simple ELISA procedure requires sample preprocessing and metering, multiple reagent additions, incubations and washings, reaction monitoring, and data acquisition and processing.

Traditionally, an ELISA procedure is performed in a single reaction chamber which contains the immobilized antibody or antigen. Aliquots of sample, reagents, wash solutions and like substances are introduced into or removed from the single reaction chamber in accordance with the processing step desired to be conducted within the chamber. It is common, however, that several steps in the procedure are performed external to the reaction chamber in preparation of various ones of the processing steps to be conducted within the chamber. Such externally-performed tests render the analysis process time-consuming and subject to errors for which an analyst may be responsible. Furthermore, during tests such as may involve an enzyme-linked immunosorbent assay (ELISA) used to detect the presence of an AIDS antibody, the analyst could be exposed to a biohazardous sample during the performance of external processing steps. It would be desirable to provide a rotor within which a relatively large number of processing steps can be automatically performed thus limiting the number of external processing steps necessary during analysis and increasing the safety of an analysis during some types of testing. In particular, it would desirable to provide a rotor system which automates all of the steps of the ELISA procedure.

Accordingly, it is an object of the present invention to provide a new and improved rotor for use during the processing of liquids.

Another object of the present invention is to provide such a rotor and method for use wherein a measured aliquot of liquid is automatically separated from an excess amount of liquid without the use of capillary tubes, moving parts supported within the rotor or manual intervention of an analyst.

Still another object of the present invention is to provide such a rotor having at least two internal chambers wherein liquid is transferred from one chamber to another without the use of transfer mechanisms internal of the rotor.

Yet another object of the present invention is to provide such a rotor having an internal passageway opening through which liquid is not permitted to pass prior to the occurrence of a predetermined event, such as the insertion of a capillary tube through the passageway opening.

A further object of the present invention is to provide such a rotor within which a relatively large number of processing steps can be automatically performed.

A still further object of the present invention is to provide such a rotor which is particularly well-suited for analyzing whole blood samples and which increases the safety of an analyst during the processing steps.

A yet further object of the present invention is to provide such a rotor whose operation is well-suited for use in micro-gravity conditions of space.

One more object of the invention is to provide rotor means for automating an enzyme-linked immunosorbent assay (ELISA) process and other, similar processes.

SUMMARY OF THE INVENTION

The present invention resides in a rotor assembly for performing processing steps upon a liquid and a method of using the assembly. The assembly includes a rotor body rotatable about an axis of rotation and having a network of chambers within which processing steps are performed upon liquid introduced within the rotor body.

In one aspect of the assembly of the invention, the rotor body is capable of separating at least one measured aliquot of liquid from an excess amount of liquid. To this end, the rotor body includes a loading chamber for receiving an excess amount of liquid, a measuring chamber for accepting a measured aliquot of liquid, and an overflow chamber for collecting at least a portion of the remaining liquid. The loading, measuring and overflow chambers are in flow communication with one another and disposed in such a relation to the rotational axis of the body so that upon rotation of the body, the liquid is centrifugally urged radially outwardly of the loading chamber and into the measuring and overflow chambers toward a condition of equilibrium at which the liquid ceases to flow between the chambers. When the liquid reaches its condition of equilibrium, an aliquot of prescribed measure is contained within the measuring chamber and is set apart from the remaining liquid. During an aspect of the method of the invention involving this rotor body, an excess amount of liquid is introduced into the loading chamber and the rotor body is rotated until the liquid reaches its condition of equilibrium.

Further describing the above aspect of the invention, the rotor body includes a loading chamber having an entrance for accepting an excess amount of a liquid, a loading chamber exit through which the liquid leaves the loading chamber, the loading chamber exit being located at a first radial distance from the axis of rotation. The rotor body further includes a measuring chamber for receiving a volumetric amount of the excess amount of liquid, the measuring chamber having a measuring chamber entrance through which the liquid enters the measuring chamber, the measuring chamber entrance being located at a second radial distance from the axis of rotation, the second radial distance being greater than the first radial distance. The rotor body further includes an overflow chamber for receiving at least a portion of the excess amount of liquid, the overflow chamber having an overflow chamber entrance through which the liquid enters the overflow chamber, the overflow chamber entrance being located a third radial distance from the axis of rotation, the third radial distance being greater than the second radial distance. The rotor body further includes fluid communication means for defining a fluid communication path between the loading chamber exit, the measuring chamber entrance, and the overflow chamber entrance, and extending to a fourth radial distance from the axis of rotation, the fourth radial distance being greater than the third radial distance. The fluid communication means has greater flow capacity to the measuring chamber than to the overflow chamber.

In another aspect of the assembly of the invention, the rotor body has a first cavity region for containing a liquid and a second cavity region disposed to one side of the first cavity region corresponding to the direction in which the rotor body is rotated about its rotational axis. The first and second cavity regions are in flow communication with one another so that when the rotor body is rotated in one direction in a manner imparting momentum to liquid contained within the first cavity region and then rapidly stopped, liquid contained within the first cavity region is transferred to the second cavity region by means of the imparted momentum. During an attending method of the invention, liquid is introduced within the first cavity region, and the rotor body is rotated in the one direction in a manner imparting momentum to the liquid contained within the first cavity region. The rotation of the rotor body is subsequently stopped rapidly so that the liquid is transferred to the second cavity region by the imparted momentum.

Further describing the above aspect of the invention, the rotor body includes a first cavity region having an outer wall at a particular radial distance from the axis of rotation, a second cavity region, and, means for diverting liquid from the first cavity region to the second cavity region when the rotor body is rotated in a manner imparting momentum to liquid contained within the first cavity region and then rapidly stopped. The liquid diverting means has an influent end positioned at the particular radial distance and is in fluid communication with the first cavity region at the influent end. The liquid diverting means also has an effluent end positioned at another, smaller radial distance from the axis of rotation, and is in fluid communication with the second cavity region at the effluent end. Between the two ends, the liquid diverting means defines a liquid flow path between the cavity regions, corresponding to the direction in which the rotor body is rotated about the axis of rotation.

In still another aspect of the present invention, the rotor body includes at least one channel having a first section for containing a liquid and a second section. The rotor assembly also includes a capillary tube having an end portion of a preselected outer diameter and means defining a passageway opening connecting the first and second sections of the channel. The opening is sized so that the surface tension of liquid contained within the first section prevents the passage of liquid through the opening and so that the end portion of the capillary tube is insertable through the opening and into the first section for extracting an amount of liquid therefrom. In a related aspect of the method of this invention, a liquid is introduced into the first section and the end portion of the capillary tube is inserted through the passageway opening so that at least a portion of the liquid moves into the capillary tube. The capillary end portion is subsequently withdrawn for transport of the liquid portion to the second section of the rotor body.

In a further aspect of the present invention, the rotor body includes at least one discrete chamber within which a processing step on a liquid is performed and a passageway communicating with the discrete chamber. The rotor assembly also includes transfer means movably positioned within the passageway for transporting a substance along the passageway to the discrete chamber and including a magnetically-attractable material. Moving means are included in the assembly for moving the transfer means along the passageway toward the discrete chamber. Such moving means includes means for generating a magnetic field adjacent the transfer means so that the magnetic influence upon the magnetically-attractable material moves the transfer means along the passageway. In a companion aspect of the method of the invention, a substance is introduced into the transfer means for transport, and the magnetically-attractable material is exposed to a magnetic field. The magnetic field is then moved along the passageway so that the magnetic influence upon the magnetically-attractable material moves the transfer means along the passageway.

In a still further aspect of the present invention, the rotor body is used in an assay technique, such as an ELISA technique, involving an amount of whole blood. For this purpose, the rotor body includes a central chamber and at least six separate chambers which are in communication with and radiate from the central chamber. Moreover, a shuttle is positioned within the rotor body and includes a body which is slidably movable through the central chamber and positionable in operative registry with any of the separate chambers. In addition, the shuttle includes a reaction cup carrying one of an immobilized antigen and antibody for transport between the separate chambers. At the outset of the technique, a whole blood sample is introduced into a first of the separate chambers, a wash solution is introduced into a second of the separate chambers, a third of the separate chambers is dedicated to drying purposes, an enzyme conjugate is introduced into a fourth of the separate chambers, a substrate solution is introduced into a fifth of the separate chambers, and a reagent reference is introduced into a sixth of the separate chambers The rotor body is then rotated to centrifugally separate the whole blood into cellular and plasma components. The rotor body rotation is subsequently stopped, and the reaction cup is positioned in operative registry with the first chamber for binding one of the immobilized antigen and antibody carried by the reaction cup with soluble antigen or antibody contained within the sample. The reaction cup is then removed from the first chamber and positioned in operative registry with the second chamber. The reaction cup is then washed in the wash solution contained within the second chamber and dried within the third chamber as the rotor body is rotated. With the rotor body rotation stopped, the reaction cup is then removed from the third chamber and positioned in operative registry with the fourth chamber for binding of the enzyme conjugate with the bound antigen/antibody complex of the plasma sample. The reaction cup is subsequently removed from the fourth chamber and positioned into operative registry with the second of the separate chambers where the cup is washed in the wash solution contained therein. The cup is thereafter positioned into registry with the third chamber for drying as the rotor body is rotated. With the rotor body rotation stopped, the reaction cup is removed from registry with the third chamber and inserted into the substrate solution contained within the fifth chamber for generation of a product for analysis. The cup is thereafter removed from the fifth chamber, and the generated product is optically monitored while rotating the rotor body and comparing the monitored product with the reagent reference contained within the sixth of the chambers.

DETAILED DESCRIPTION OF THE PREFERRED EMBODIMENTS.

Figure 1:
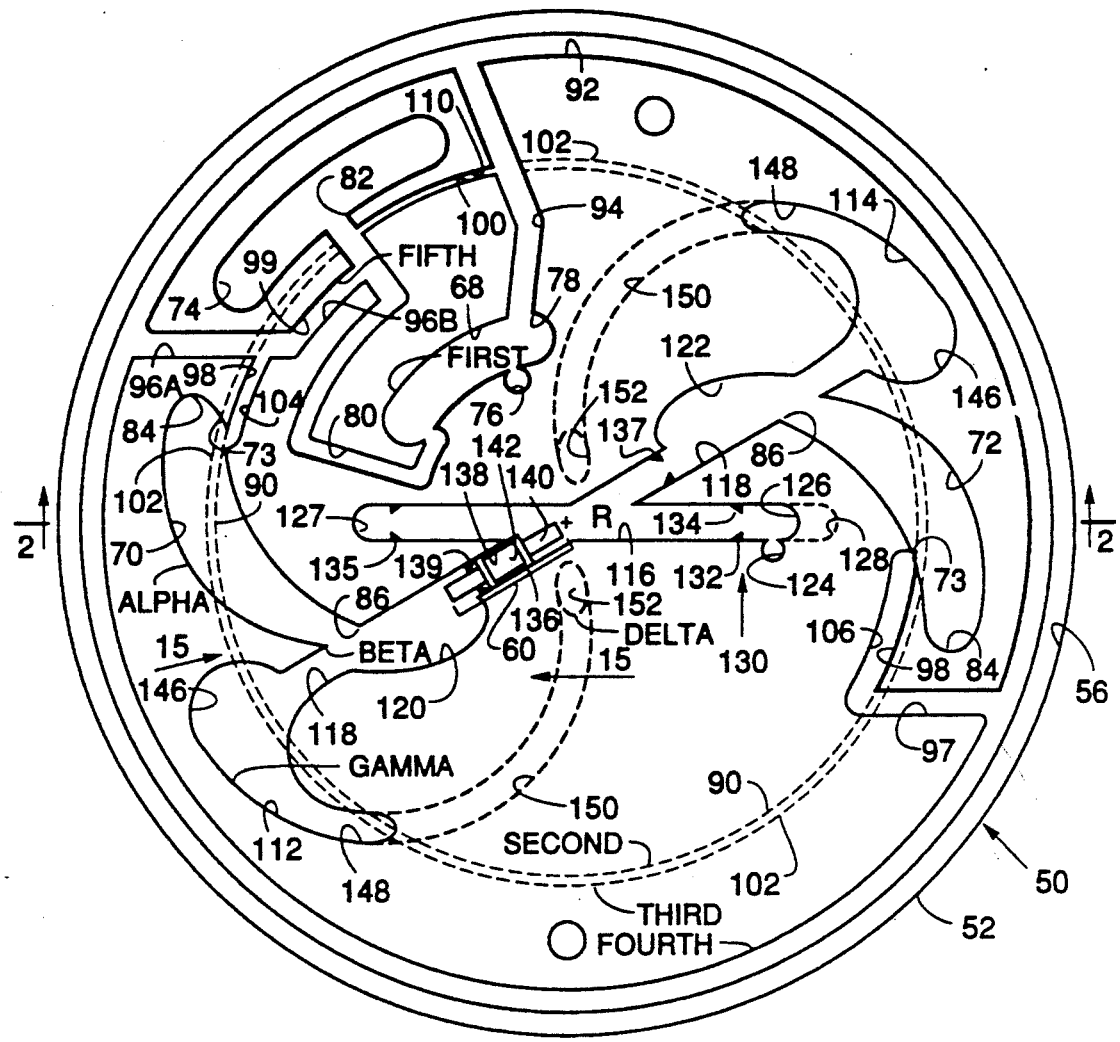
FIG. 1 is a plan view of a rotor body of one assembly embodiment of the present invention shown with the top plate removed.
Figure 2:
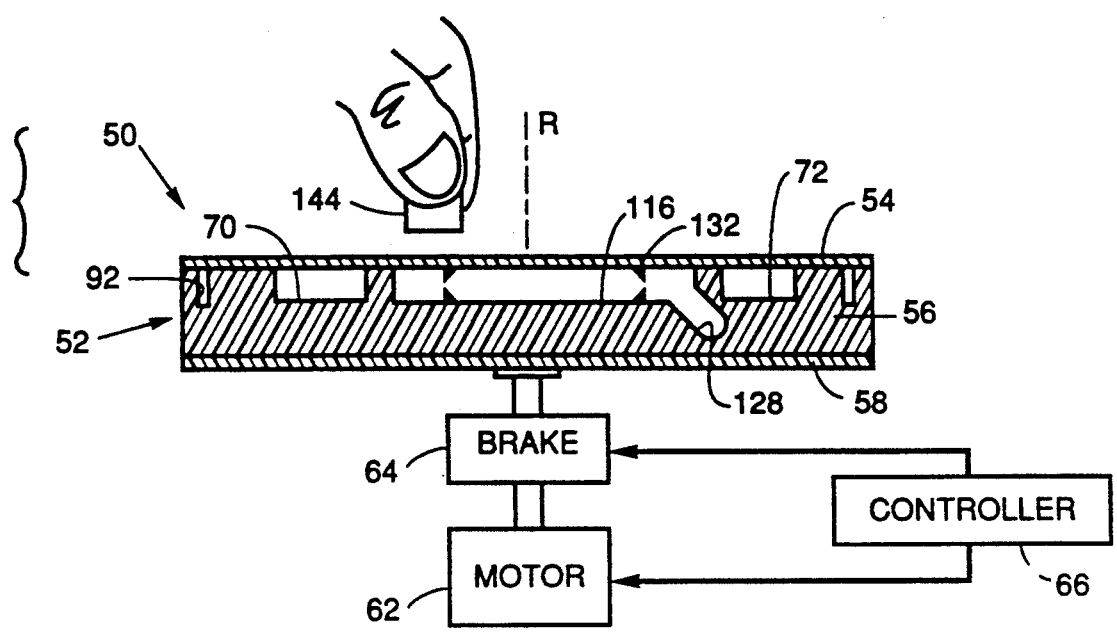
FIG. 2 is a cross-sectional view taken about on line 2—2 of FIG. 1 and illustrating in schematic form components for operating the FIG. 1 rotor body.

In FIGS. 1 and 2, there is shown a rotor assembly 50 including a rotor body 52 capable of rotation about a vertical axis R. The rotor body 52 includes a top plate 54 (removed in FIG. 1 for clarity), a central plate 56, and a bottom plate 58 sealingly attached to one another. As best shown in FIG. 1, the central plate 56 includes a network of passageways and cavities which provide a plurality of channels and interconnecting chambers through the body 52. During selected stages of operation of the rotor assembly 50, liquid contained within the rotor body 52 is moved through the body passageways or chambers by either centrifugal forces exerted upon the liquid during rotation of the body 52, by rotational momentum imparted to the liquid a the rotation of the body 52 is suddenly halted, or means of a transfer mechanism 60, described hereinafter, capable of being moved between preselected positions within the rotor body passageways.

The rotor assembly 50 is described herein for use during the performance of a number of processing steps upon a sample of blood. Such processing steps include, for example, the separating of blood serum from blood cells, drawing a specific aliquot of the serum, diluting the aliquot of the blood serum with a specific amount of diluent and delivering the diluted serum to an analytical test pad or other analysis device. It will be understood, however, that the rotor assembly 50 described herein can be used for processing other liquids or fluids for evaluation. Accordingly, the principles of the present invention may be variously applied.

With reference to FIG. 2, the rotor body 52 is rotated by about the axis R by means of a reversible motor 62 capable of spinning the rotor body 52 at various rotational speeds. Braking means 64 are appropriately coupled to the rotor body 52 on motor 62 for abruptly halting the rotation of the body 52 when the body rotation is desired to be stopped suddenly. For purposes of automatically controlling the initiation, speed and braking of rotor body rotation, a controller 66 is coupled to the motor 62 and braking means 64.

Figure 29:
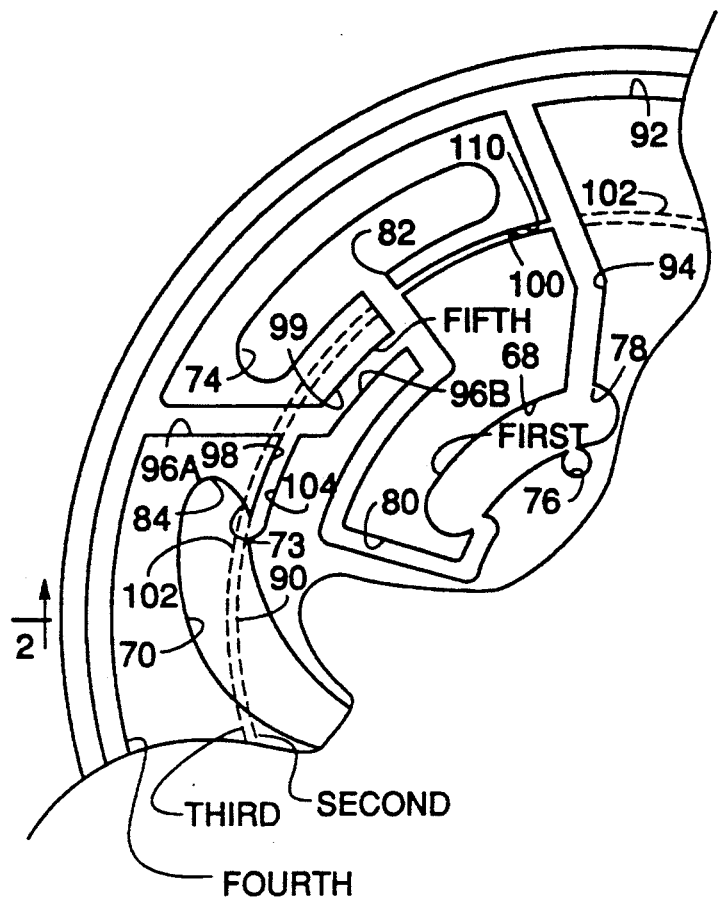
FIG. 29 is a cut-away view of the rotor assembly of FIG. 1 illustrating features related to the separation of a volumetric amount of liquid from an excess amount of liquid.
Figure 30:
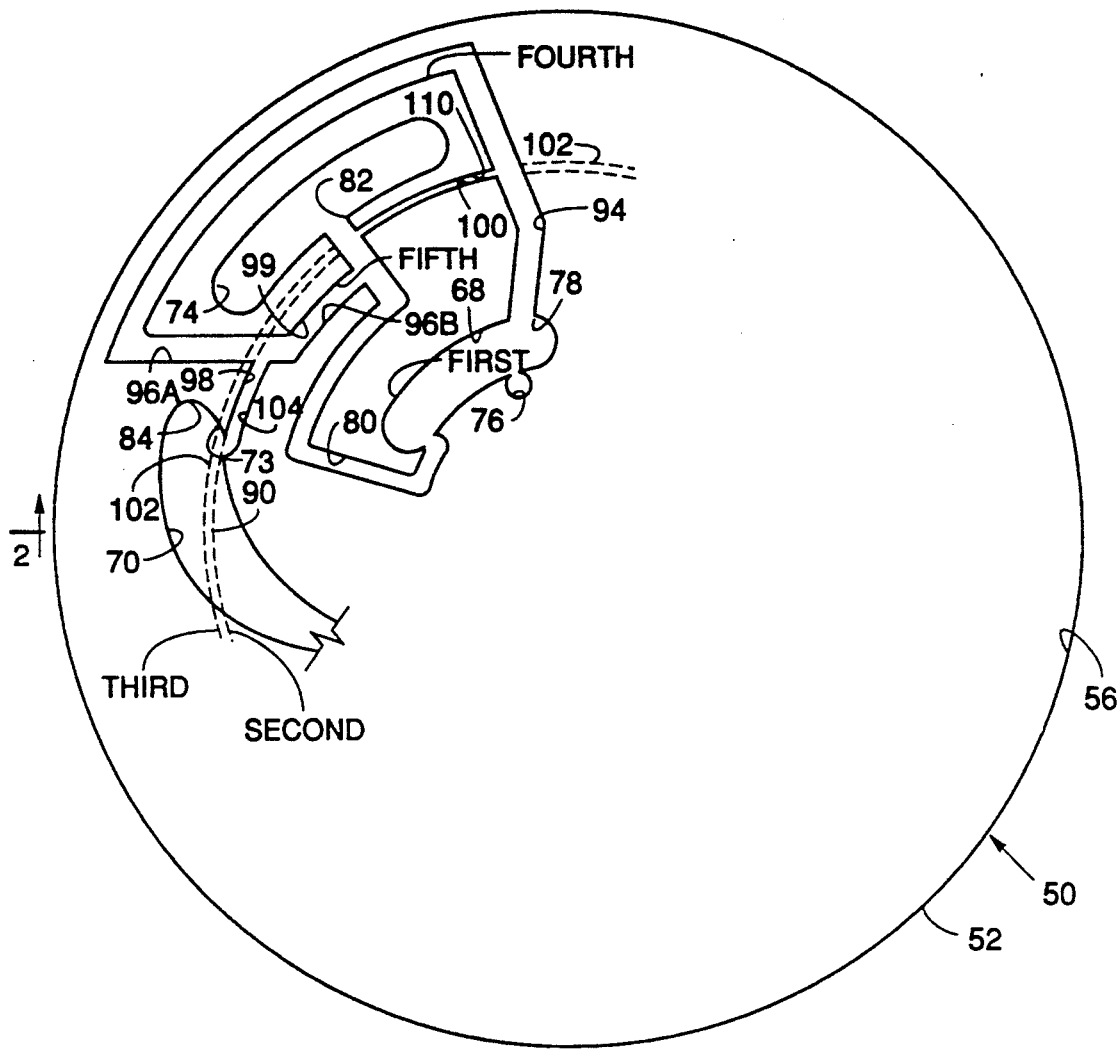
FIG. 30 is a plan view of a stand-alone rotor assembly embodiment similar to the cut-away view shown in FIG. 29.

For purposes of diluting a portion of a blood sample with an aliquot of diluent of a prescribed measure, the rotor body 52 includes means by which at least one aliquot of prescribed volume can be separated from an excess amount of diluent introduced within the rotor body 52. In this connection and with reference again to FIG. 1, the cavities and passageways of the rotor body 52 are shaped so as to provide one loading chamber 68, two measuring chambers 70, 72, and one overflow chamber 74. The loading, measuring and overflow chambers 68, 70, 72, 74 are connected in flow communication and are disposed in such a relationship to one another and to the rotational axis R so that the centrifugal forces generated during rotation of the body 52 move the diluent from the loading chamber 68 radially outwardly toward a condition of equilibrium at which the liquid ceases to move, under the effects of centrifugal force, through the body 52 and so that a measured aliquot of diluent is contained within each of the measuring chambers 70, 72 and separated from the remaining diluent. Pertinent views of this particular aspect of the invention are also found in FIGS. 29 and 30.

As shown in FIG. 1, the loading chamber 68 includes a cavity section having an entrance in flow communication with a port 76 which opens through the top plate 54. It is through the port 76 that the diluent is introduced into the cavity section with a hypodermic needle (not shown) or other suitable means. In order that the amount of diluent introduced into the loading chamber can be divided into two aliquots having volumes which correspond to the volumetric measures desired to be isolated within the measuring chambers 70, 72, the amount of diluent introduced through the port 76 is at least as great as the combined volumes of the aliquots expected to be isolated plus that of channels 92, 96A and 97, described herein. Accordingly, the loading chamber 68 is large enough to accept the amount of introduced diluent.

The loading chamber 68 also includes an exit 78 located at a particular radial distance from the axis of rotation, and through which the diluent leaves the chamber 68 when the rotor body 52 is rotated about the axis R. As best shown in FIG. 1, the exit 78 is located along a radially-outermost wall of the loading chamber 68 so that sufficient rotation of the rotor body 52 drains the diluent from the loading chamber 68. A vent channel 80 extends between the overflow chamber 74 and loading chamber 68 permits air to replace the diluent exiting the loading chamber 68 as the rotor body 52 is rotated. In order that no diluent is forced into the vent channel 80 from the loading chamber 68 as the body 52 is rotated, the vent channel 80 opens into the loading chamber 76 along a radially-innermost wall thereof.

The overflow chamber 74 is disposed radially outwardly of the, loading chamber 68 and includes a cavity section for collecting diluent and an entrance 82 which terminates at a particular radial distance 102 from the axis rotation, or through which diluent is permitted to pass as the body 52 is rotated. As shown in FIG. 1, the entrance 82 is disposed along a radially-innermost wall of the overflow chamber 74.

Like the overflow chamber 74, each measuring chamber 70 or 72 is disposed radially outwardly of the loading chamber and includes a cavity section for collecting diluent and an entrance 73 located at a particular radial distance 90 from the axis of rotation, and through which diluent is permitted to pass as the body 52 is rotated. Each measuring chamber 70 or 72 is elongated in shape with two opposite ends 84 and 86 and has an exit disposed at the end 86 which is directed generally in the direction of counterclockwise rotation, as viewed in FIG. 1, of the body 52 and positioned radially inwardly of the chamber end 84 and the measuring chamber entrance 73. For a reason apparent herein, the floor of each measuring chamber 70 or 72 slopes upwardly, when viewed in elevation as in FIG. 2, toward the exit end 86.

Each measuring chamber 70 or 72 is shaped so that when the level of the diluent, as measured radially across the body 52 from the axis R, is about equal to the distance at which the measuring chamber entrance 73 is positioned from the axis R, the chamber 70 or 72 contains the aliquot of prescribed measure. Accordingly, the volumetric capacity of the measuring chamber 70 or 72 as measured between its radially outwardmost wall and an imaginary wall which corresponds to the distance 90 at which the measuring chamber entrance 73 is spaced from the rotation axis R is equal to the volume of the measured aliquot.

The loading chamber 68, overflow chamber 74 and measuring chambers 70, 72 are joined in communication with one another by channels extending through the body 52. Such channels include a circular distribution channel 92 disposed radially outwardly of each of the chambers 68, 70, 72, 74 adjacent the periphery of the body 52 so that the center of the circle formed by the distribution channel 92 is coincident with the rotation axis R. Another such channel, indicated 94, extends generally radially outwardly of the body 52 from the exit 78 of the loading chamber 68 to the distribution channel 92, and other such channels 96A, 97 extend generally radially inwardly of the body 52 from the distribution channel 92 to a position radially inwardly of the overflow and the measuring chambers 70, 72, 74. In addition, the vent channel 80, introduced earlier, extends radially inwardly of the body 52 from the entrance 82 of the overflow chamber 74, and an overflow channel 96B extends between the channel 96A and the vent channel 80 as shown in FIG. 1.

The radially-extending channel 94 and the vent channel 80 are joined in communication by means of a narrow channel 100 having a radially-outermost wall 110 which is spaced at a constant distance 102 from the axis R. The entrance 73 of each measuring chamber 70 or 72 communicates with a corresponding channel 96A or 97 by means of an entryway channel 104 or 106 each having a radially-outermost wall 98 which extends along a path spaced a constant distance from the rotation axis R. More specifically, the distance at which the outermost wall 98 of each entryway channel 104 or 106 is spaced from the axis R corresponds to the distance 90 at which the entrance 73 of each measuring chamber 80 or 72 is spaced from the axis R. In addition, each entryway channel 104 or 106 is appreciably larger in cross section than that provided by the narrow channel 100 for a purpose apparent herein, and the channel 96B has a radially-outermost wall 99 which is positioned radially inwardly of the outermost wall 98 of each entryway channel 104 or 106 and the narrow channel 100.

Figure 3:
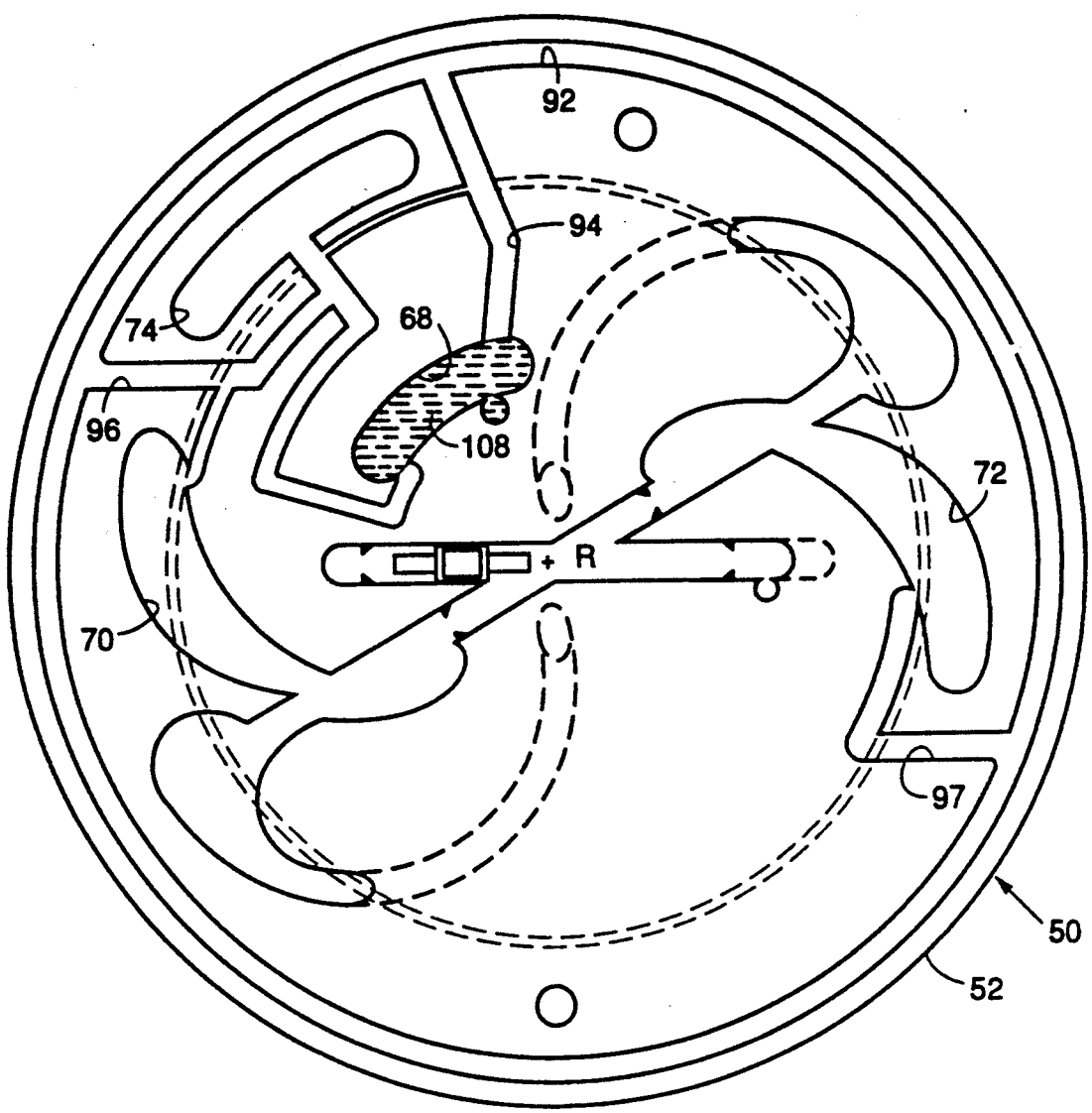
FIG. 3 is a view similar to that of FIG. 1 illustrating the condition of diluent in the rotor body when introduced therein.
Figure 4:
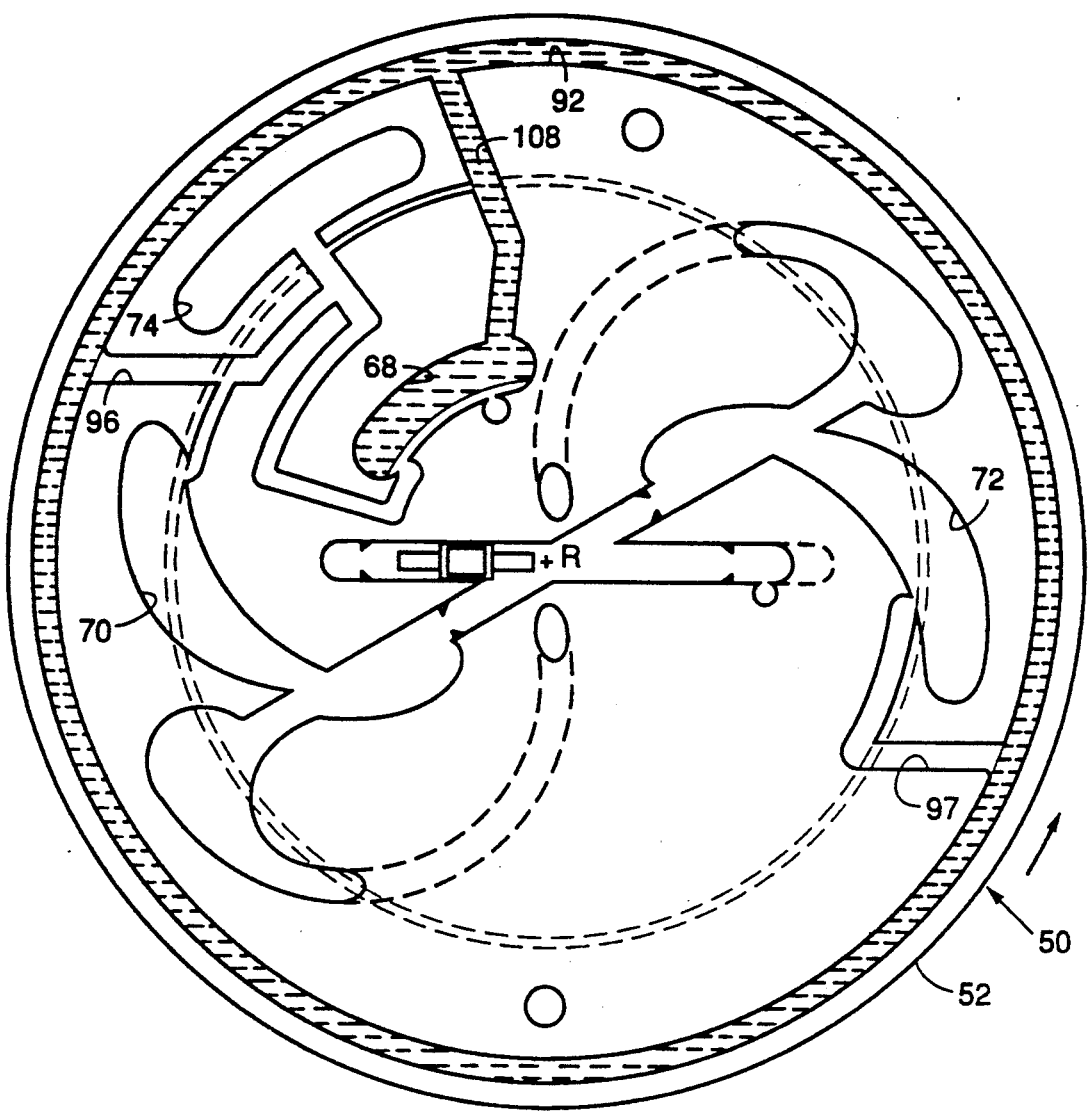
FIGS. 4–6 are views similar to that of FIG. 3 illustrating in sequence the various conditions of diluent in the rotor body when rotated and before the diluent reaches a condition of equilibrium.
Figure 5:
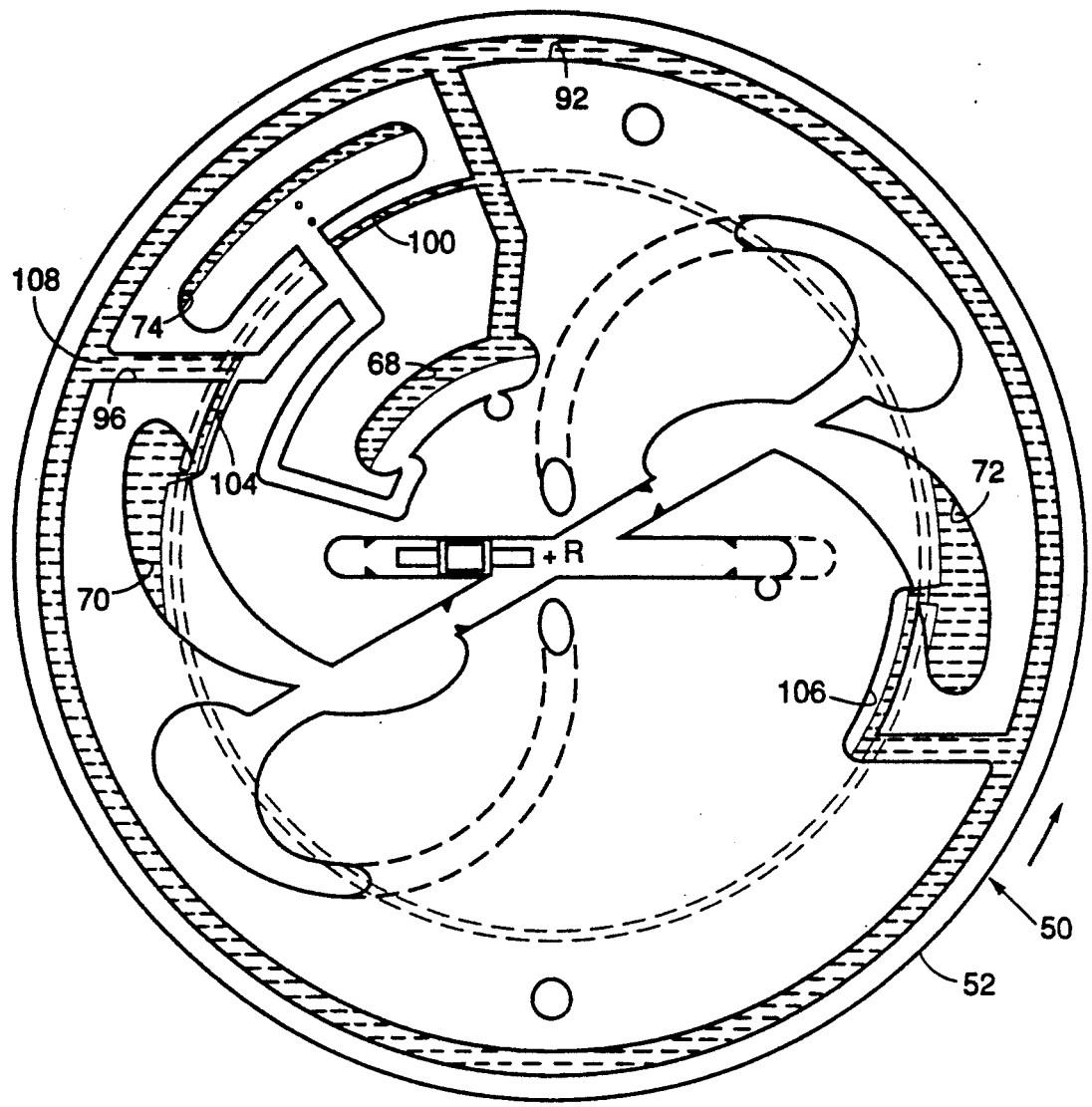

To use the rotor assembly 50 for separating two aliquots of prescribed measure from an excess amount of diluent and with reference to FIG. 3, the excess amount of diluent 108 is introduced within the loading chamber 68 through the port 76 while the rotor body 52 is stationary. The body 52 is then rotated so that the diluent 108 flows radially outwardly of the body 52 toward the distribution channel 92 and so that the channel 92 is filled with diluent as shown in FIG. 4. Once the distribution channel 92 is filled to capacity, the diluent 108 is forced to move radially inwardly along the channels 94, 96A, and 97 toward the entryway channels 104, 106 as the levels of the diluent 108, as measured radially across the body 52 from the axis R, throughout the body channels seek a condition of positional equilibrium, or a condition at which the diluent ceases to flow between the chambers 68, 70, 72. Once the diluent reaches the entryway channels 104, 106 as shown in FIG. 5, the diluent 108 flows through the channels 104, 106 and fills the measuring chambers 70, 72 through the entrances thereof. Diluent 108 is permitted to migrate into the overflow chamber 74 through the narrow channel 100 as the measuring chambers 70, 72 are being filled with diluent, but due to the size difference between the entryway channels 104, 106 and narrow channel 100 only a relatively small amount of diluent 108 flows through the relatively narrow channel 100 in comparison to the amount of diluent permitted to flow through the entryway channels 104, 106.

Figure 6:
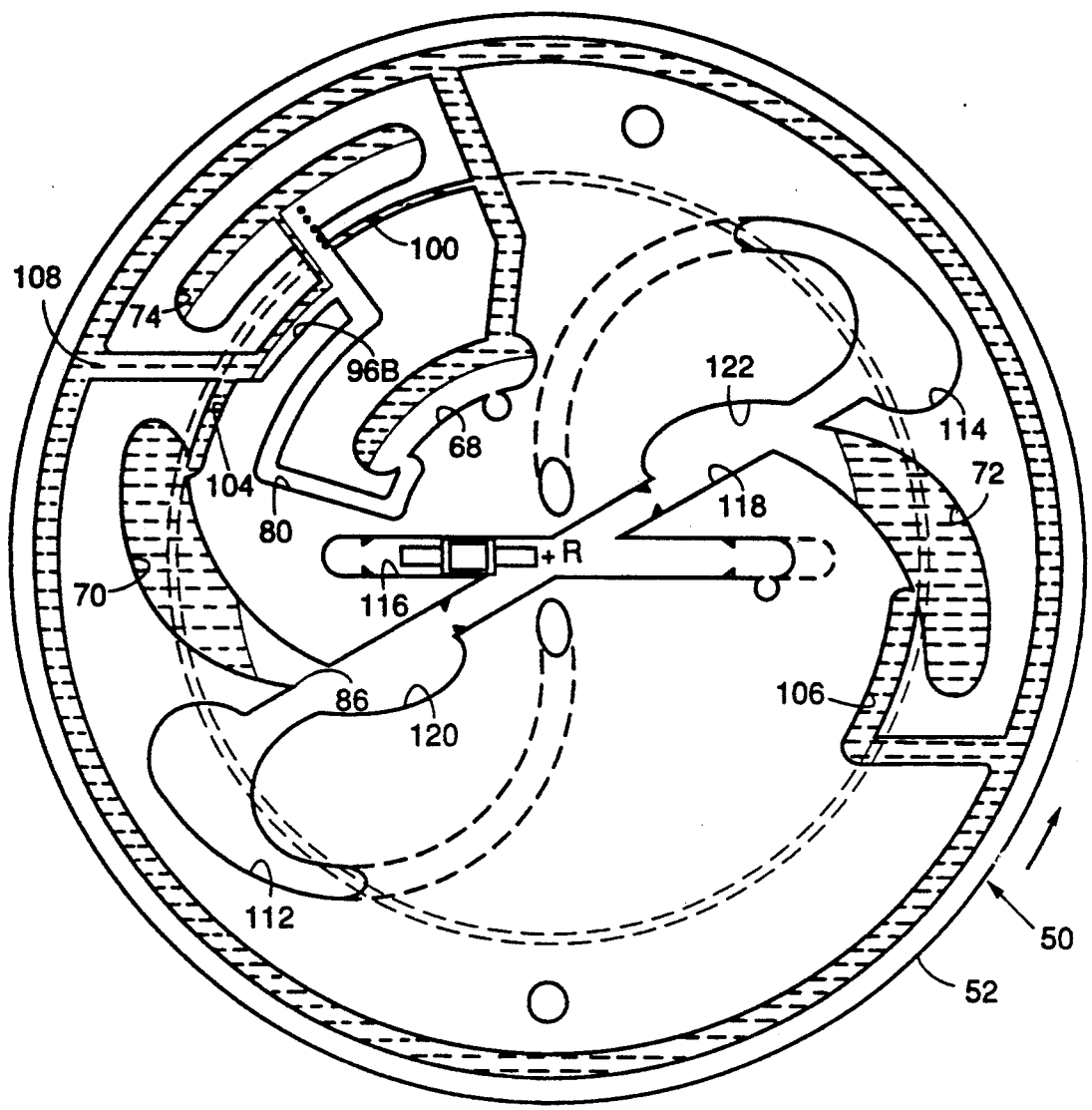
Figure 7:
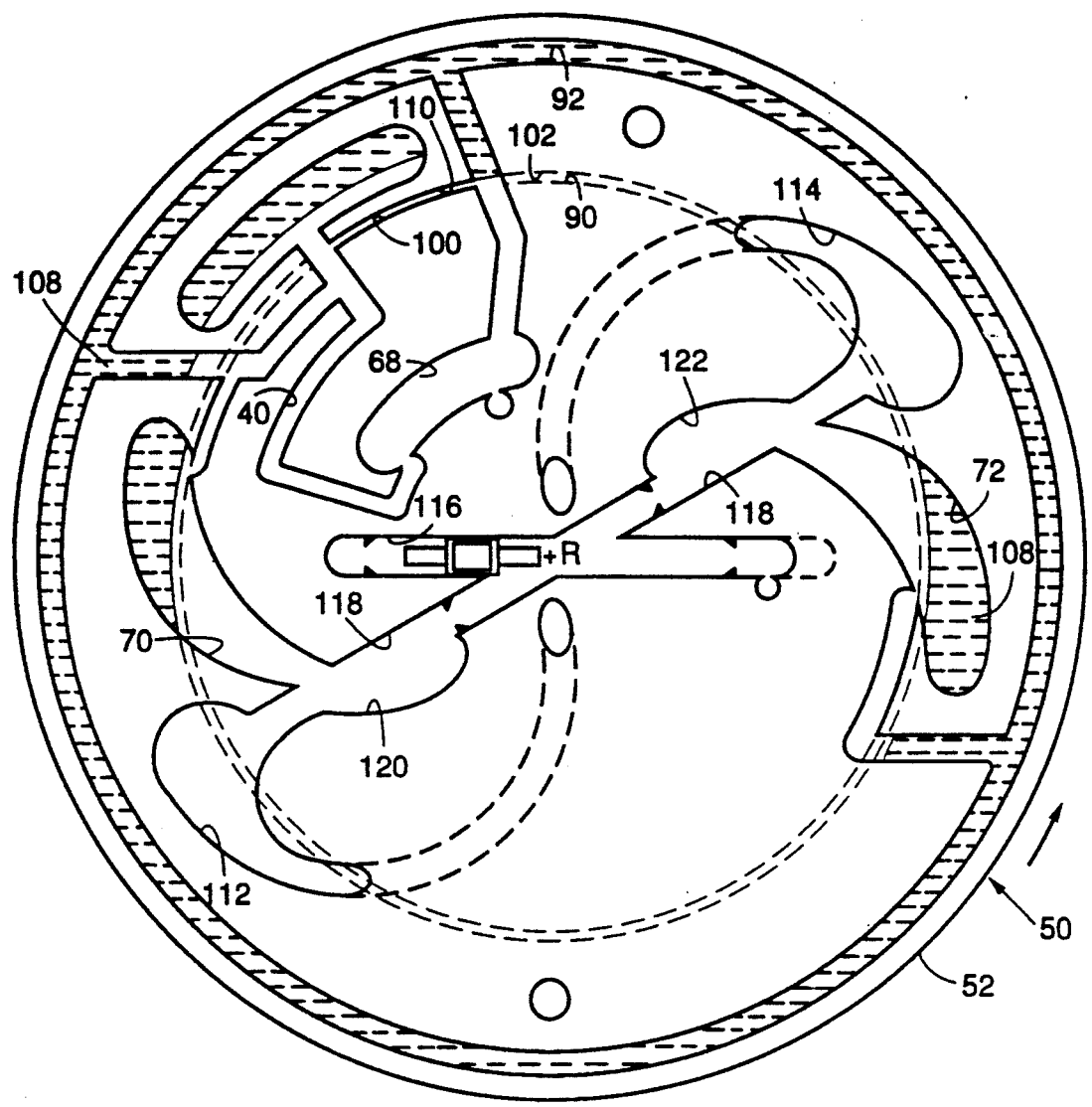
FIG. 7 is a view similar to that of FIG. 3 illustrating the condition of diluent upon reaching a condition of equilibrium.

The measuring chambers 70, 72 continue to fill with diluent 108 and the diluent continues to move inwardly of the channel 94 to the overflow, or spill over channel 96B, as shown in FIG. 6, where the diluent is permitted to flow at an increased rate into the overflow chamber 74. Because the exit end 86 of each measuring chamber 70 or 72 is positioned radially inwardly of the outwardmost wall 99 of channel 96B, the channel 96B prevents the radial level of diluent in the measuring chambers 70, 72 from reaching the exit end 86. As the diluent 108 continues to seek its condition of equilibrium, it continues to flow through the narrow channel 100 to the overflow chamber 74 as diluent drains out of the measuring chamber entrance 73 through the entryway channels 104, 106. When the diluent finally reaches its condition of equilibrium, as shown in FIG. 7, the narrow channel 100 has drained the diluent from the measuring chambers 70, 72 back to the radius of channel wall 98 so that the quantity of diluent remaining in each measuring chamber 70 or 72 corresponds with that of the desired aliquot and so that each aliquot is physically separated from any other diluent in the rotor body 52. It follows that two aliquots of diluent are separated from the excess amount of diluent without the use of capillary tubes, moving parts supported within the rotor or manual intervention of an analyst.

With reference again to FIG. 1, the rotor body 52 includes a pair of mixing chambers 112, 114 and is adapted to transfer, upon the sudden halting of the rotation of the body 52, its measured aliquots of diluent to the mixing chambers 112, 114 where, for example, each aliquot can be mixed with a portion of a blood sample in a manner described hereinafter. In this connection, the rotor body 52 includes a pair of linear passageways or channels 116, 118 which intersect one another in the vicinity of the axis R, and one channel 118 communicates with the exit end 86 of each measuring chamber 70 or 72 and the mixing chambers 112, 114, as shown in FIG. 1. In addition, each measuring chamber exit end 86 is joined to the channel 118 at a location positioned generally between the corresponding axis R and the corresponding mixing chamber 112 or 114. Furthermore, there is defined along the wall of channel 118 at locations generally opposite the measuring chamber exits a pair of cutouts 120, 122. The floor of each channel passageway cutout 120 or 122 is below the horizontal level of the exit end 86 to reduce any likelihood of liquid flow from the cutouts 120, 122 back into the measuring chamber exits 86.

Figure 8:
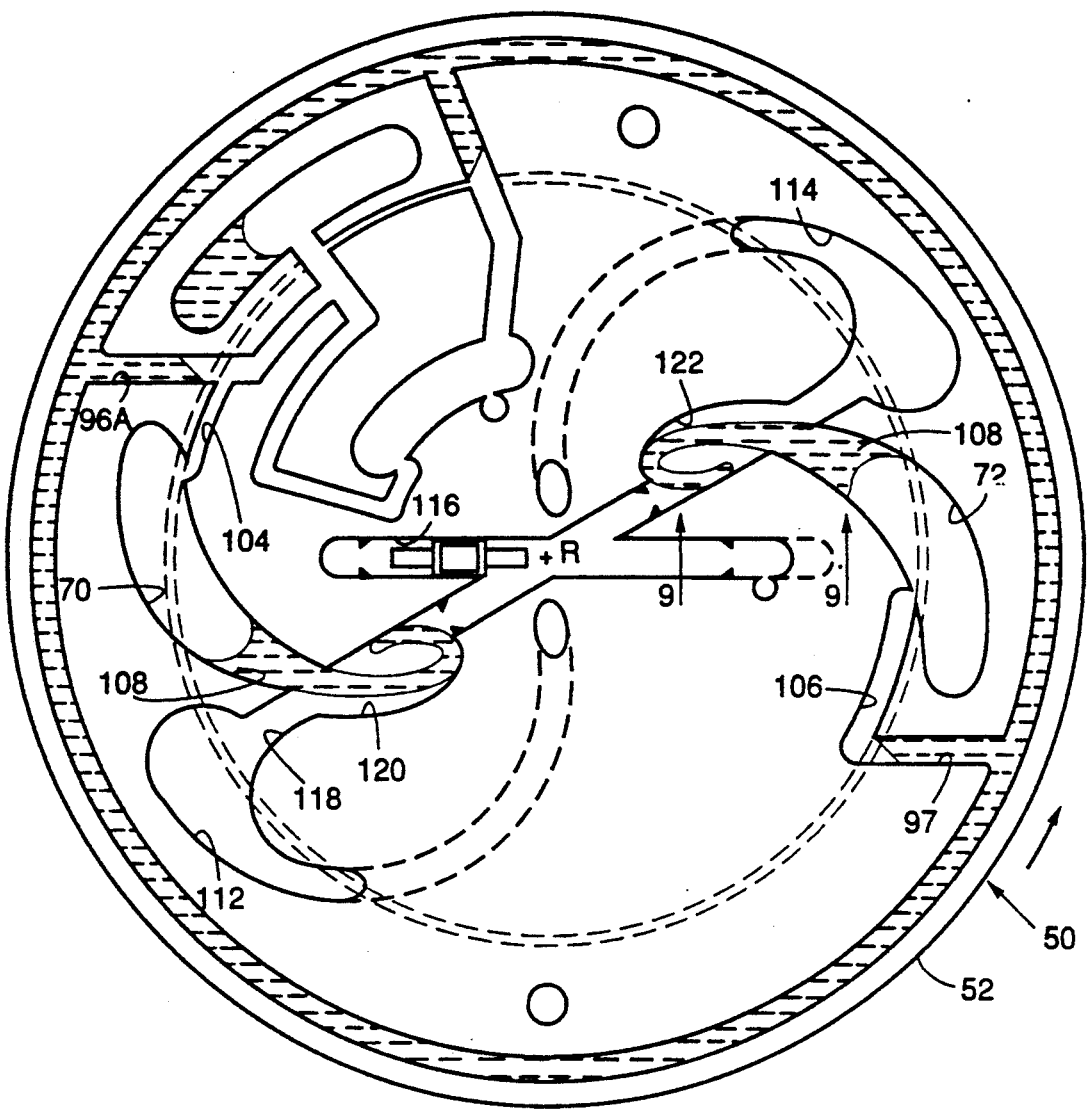
FIG. 8 is a view similar to that of FIG. 3 illustrating the condition of diluent when the rotation of he rotor body is abruptly stopped.
Figure 9:
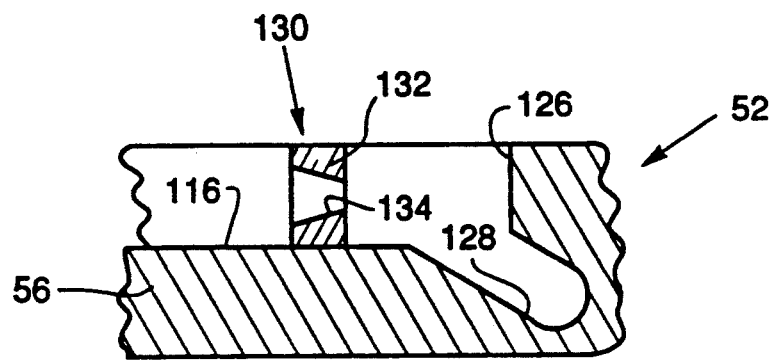
FIG. 9 is a fragmentary cross-sectional view taken about on line 9—9 of FIG. 8.

To transfer the diluent 108 from the measuring chambers 70, 72 to the mixing chambers 112, 114, the rotor body 52 is rapidly braked to a stop from a rotation in the counterclockwise direction as viewed in FIG. 1. The aforedescribed transfer is effected as the momentum imparted to the diluent 108 contained within each measuring chamber 70 or 72 during rotation urges the diluent through the chamber exit end 86 when the rotation of the body 52 is abruptly halted. As the diluent 108 exits each measuring chamber end 86, the cutouts 120, 122 defined along the walls of the channel 118 serve to direct the diluent toward the corresponding mixing chamber 112 or 114, as shown in FIG. 8. Subsequent rotation of the body 52 centrifugally urges any diluent which remains within the cutouts 120, 122 out into the corresponding mixing chambers 112 or 114, as shown in FIG. 9. To ensure that the excess diluent contained within channels 96A, 97 cannot flow forward into the entryway channels 104, 106 and into the aliquoted diluent which is exiting measuring chambers 70, 72 when the rotation of the body 52 is suddenly stopped as aforedescribed, channels 96A, 97 leading to the entryway channels 104, 106 are appropriately slanted as shown in FIG. 8. It follows from the foregoing that the diluent is transferred from each measuring chamber 70 or 72 to a corresponding mixing chamber 112 or 114 without the use of transfer mechanisms internal of the rotor body.

Figure 33:
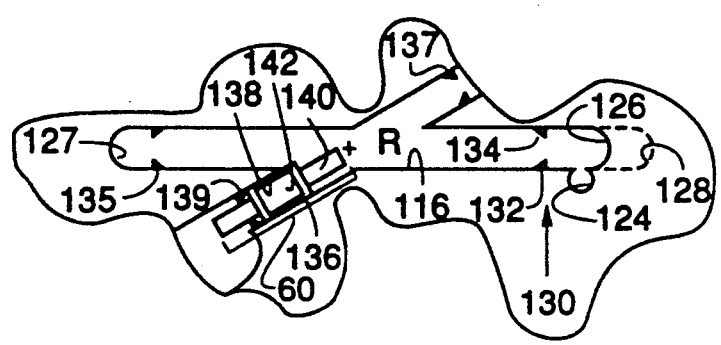
FIG. 33 is a cut-away view of the rotor assembly of FIG. 1 illustrating features related to the capillary measuring assembly.
Figure 34:
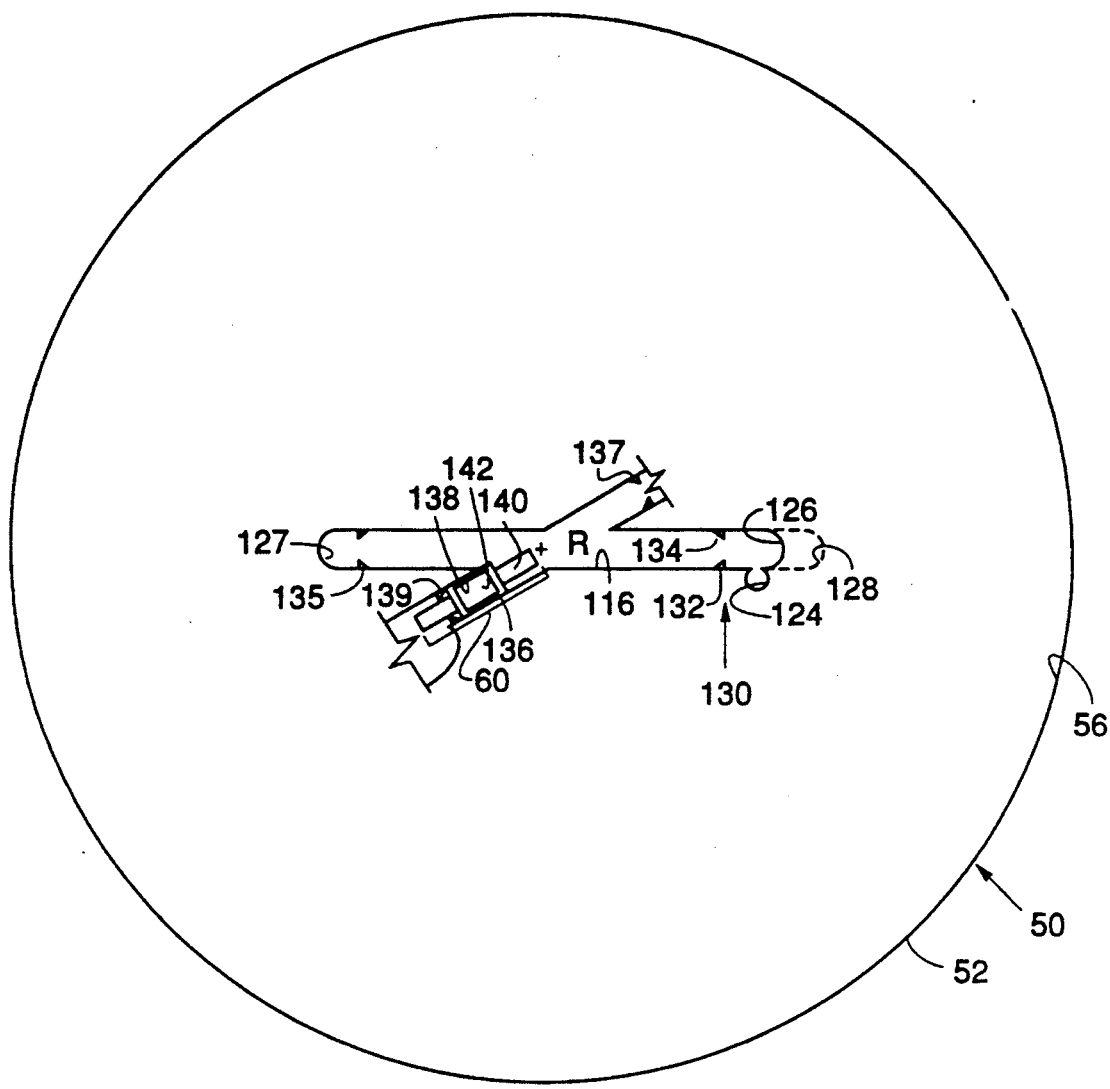
FIG. 34 is a plan view of a stand-alone rotor assembly embodiment similar to the cut-away view shown in FIG. 33.

The diluent 108 contained within each mixing 112 or 114 chamber is mixed with an amount of liquid sample introduced therein. In this connection and with reference again to FIG. 1, a port 124 is associated with one end, indicated 126, of the channel 116 permitting the introduction of a sample, such as a whole blood sample, into the channel 116. As shown in FIG. 9, the channel 116 is sloped downwardly and radially outwardly adjacent the channel end 126 so as to provide a collection reservoir 128 for the sample introduced through the port 124. The channel end 126 is spaced from the rotation axis R so that the sample contained within the reservoir 128 is exposed to centrifugal forces generated during the rotation of the body 52. Such a disposition of the reservoir 128 relative to the axis R is advantageous in that it permits a centrifugal separation (e.g., precipitation) process to be performed upon the sample while the sample is contained within the reservoir 128. For present purposes, only the blood serum of a whole blood sample is desired to be subsequently transferred to a mixing chamber for mixing with the diluent contained therein. Therefore, the rotor body 52 is rotated at high speed so that the whole blood sample is separated into its cellular and serum components. The rotor is subsequently slowed to a stop and an amount of the serum is transferred by the transfer mechanism 60, introduced earlier, to the mixing chambers 112, 114 in a manner described herein. Pertinent views of this particular aspect of the invention are also found in FIGS. 33 and 34.

In accordance with the present invention, the rotor body 52 includes means, indicated by directional arrow 130 in FIGS. 1 and 9, for preventing the sample from exiting the reservoir 128 when the rotation of the rotor body 52 is stopped. Such preventing means 130 are provided by an inwardly-projecting ring 132 attached to the walls of the channel 116 and positioned adjacent the channel end 126. The ring 132 provides a funnel-shaped opening 134 arranged so that the smaller end of its funnel is directed radially outwardly, and the passageway through the opening 134 is of such size that the sample contained within the reservoir 128 is prevented from passing therethrough by the surface tension of the liquid sample across the opening 134. At the same time, the opening 134 permits the passage of an appropriately-sized capillary tube of the transfer mechanism 60, described herein, so that one end of the capillary tube can be inserted through the opening 134 and positioned into contact with the sample contained within the reservoir 128. Therefore, the funnel-shaped opening 134 acts as a barrier through which the sample cannot exit the reservoir 128, absent a capillary tube, its funnel-like shape guides the end of a capillary tube through the opening 134 to the reservoir 128, and it provides a limit to the insertion depth of the capillary tube 140 into the reservoir 128 by acting as a stop for the holder body 138.

For preventing flow of diluent or a portion of the sample through various sections the channels 116, 118, additional rings 135, 137, 139 defining funnel-shaped openings are positioned adjacent the end of the channel 116 opposite the reservoir 128 and at two locations within the channel 118 disposed radially inwardly of the cutouts 120 and 122, as shown in FIG. 1.

Figure 10:
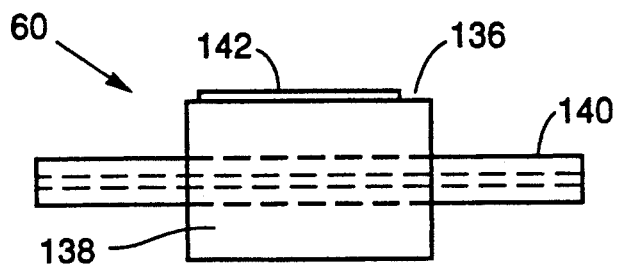
FIG. 10 is a side elevational view of the capillary measuring assembly of the FIG. 1 assembly drawn to a larger scale.

As best shown in FIG. 10, the transfer mechanism 60 is in the form of a measuring capillary assembly 136 utilized for transferring a substance from one region of the rotor body 52 to another region of the rotor body 52. The assembly 136 includes a holder body 138 which is positioned within the channel 116 for sliding movement therealong, and a straight capillary tube 140 of predetermined length and cross-sectional area supported within the holder body 138 so as to extend along the longitudinal axis of the channel 116 within which the assembly 138 is positioned. The capillary tube 140 is open at each of its two ends for a purpose apparent herein. The holder body 138 is sized so that it can be slidably moved along either channel 116 or 118 for positioning of the capillary tube 140 at a desired location therealong. Accordingly and as shown in FIG. 1, the channels 116 and 118 provide sufficient space in the vicinity of intersection to accommodate a manipulation of the capillary assembly 136 from one channel 116 or 118 into the other channel 118 or 116.

To facilitate the movement of the capillary assembly 136 along the length of a channel 116 or 118, a magnetically-attractable strip 142 is incorporated within the holder body 138 so that, when desired, the assembly 136 can be moved bodily along the length of the channel 116 or 118 by appropriate manual or automatic manipulation of a magnet or electromagnet 144 (FIG. 2) external to the rotor body 52. By placing the magnet 144 adjacent the top plate 54 of the rotor body 52 and moving the magnet 144 along the channel of desired movement, the magnetic influence of the magnet 144 upon the magnetically-attractable strip 142 moves the capillary assembly 136 along the channel.

In order to utilize the capillary assembly 136 to transfer the sample contained within the reservoir 128 into another region of the rotor body 52, the assembly 136 is guided along the channel 116 and through the funnel-shaped opening 134 of the ring 132 so that one end of the capillary tube 140 contacts the sample contained within the reservoir 128. Upon contacting the end of the tube 140, the sample enters and fills the capillary tube 140 by capillary action. Because the length and internal cross-section of the capillary tube 140 are known, the amount of sample contained within the filled tube 140 is, of course, also known.

At that point, the capillary assembly 136 is moved along the channel 116 to another region of the rotor body 52 at which the contents of the capillary tube 140 are discharged by rapidly rotating the body 52 so that the contents of the capillary tube 140 are centrifugally urged into a desired region of the rotor body 52. If, for example, the tube contents ar desired to be discharged into the end 127 of the channel 116, the capillary assembly 136 is moved, by means of the magnet 144, along the channel 116 until the holder body 138 abuts the ring 135 and an end of the capillary tube 140 extends through the opening provided in the ring 135. At that point, the rotor body 52 is rapidly rotated so that the centrifugal forces generated by the body rotation expels the tube contents outwardly of the tube 140 and into the channel end 127.

Similarly, if the tube contents are desired to be discharged into either of the mixing chambers 112, 114 of the body 52, the filled capillary assembly 136 is appropriately moved into channel 118 so that the holder body 138 abuts a corresponding ring 137 or 139 and an end of the capillary tube 140 extends through the opening provided in the corresponding ring 137 or 139. The rotor body 52 is then rapidly rotated so that the tube contents are centrifugally discharged from the tube 140 toward the chamber 112 or 114. It follows that the rings 132, 135, 137, 139 are advantageous for providing abutment stops for limiting the radially-outward movement of the capillary assembly 136 along the channels 116 and 118 as well as preventing passage of a fluid through the openings provided thereby absent the insertion of a capillary tube through the openings.

Figure 11:
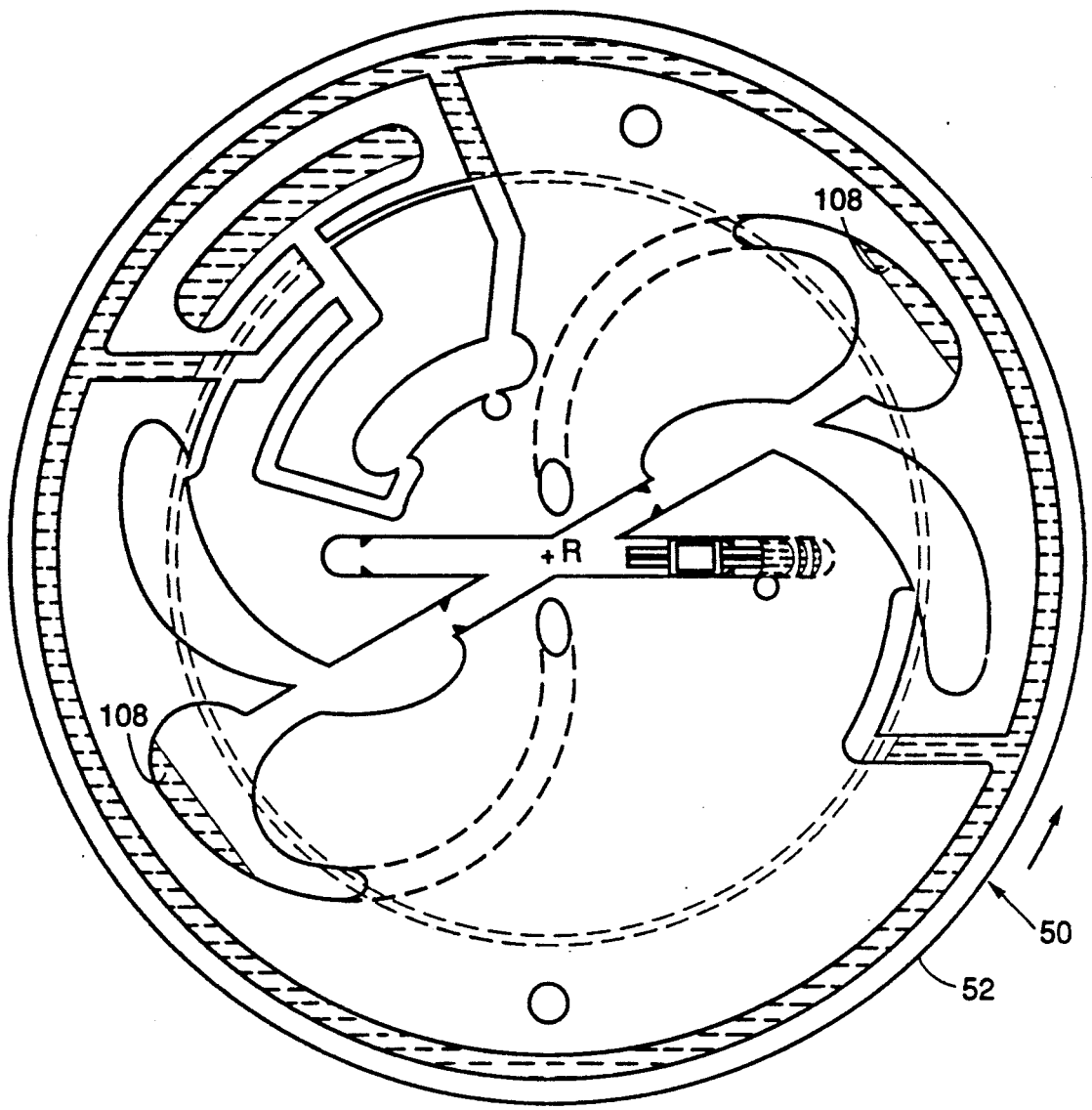
FIGS. 11–14 are views similar to that of FIG. 3 illustrating the sequential positions of the capillary measuring assembly when used to transport a serum sample to various regions of the rotor body.
Figure 12:
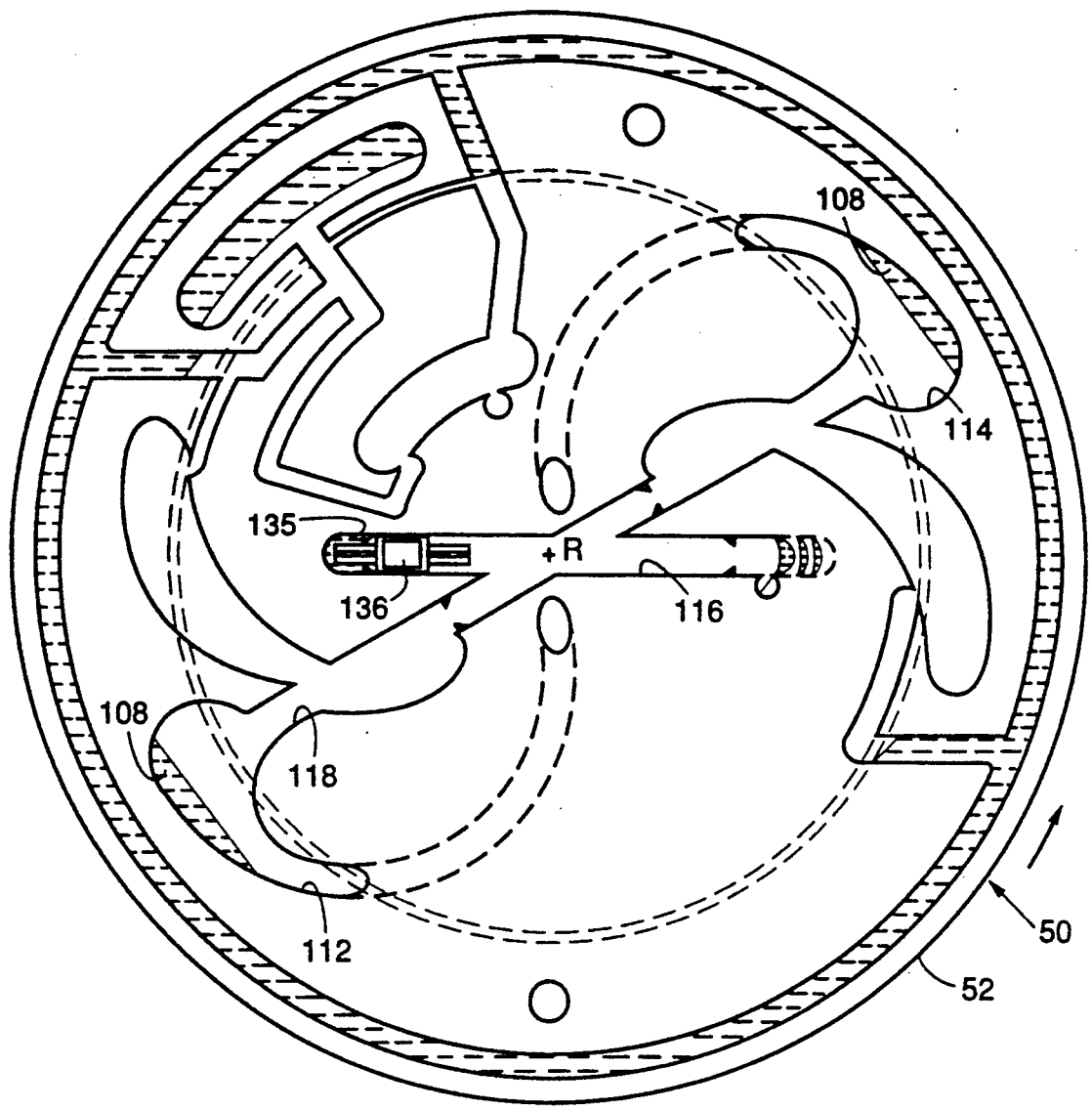

In an analysis procedure involving a whole blood sample introduced within the reservoir 128 and separated into its cellular and serum components by a high-speed rotation of the rotor body 52, the capillary assembly 136 is useful for transporting a prescribed amount of serum to the end 127 of the channel at which precipitation is performed upon the serum or to the mixing chamber 112 or 114 at which the serum is mixed with the measured aliquot of diluent 108 positioned therein. For transporting purposes, an end of the capillary tube 40 is moved through the ring 134 and into contact with the serum contained within the reservoir 128 so that the tube 40 fills by capillary action as shown in FIG. 11. In anticipation of a precipitation processing step, the end 127 of the channel 116 contains a preloaded precipitating solution so that subsequent unloading of the serum from the tube 40 into the channel end 127 by high-speed rotation of the rotor body 52 initiates the desired mixing of the serum with the precipitating solution. As shown in FIG. 12, channel 116 is of appropriate size and shape so that during the spinning action of the rotor body 52, the contents within the channel end 127 are held away from the outwardmost end of the capillary tube 40. Upon slowing the rotation of the body 52, gravity overcomes the centrifugal force acting on the liquid contents of the channel end 127 so that it tends to gather on the floor of the channel 116. Eventually, desired supernate will contact the end of the tube 40 so that the tube 40 fills with a predetermined amount of supernate.

Figure 13:
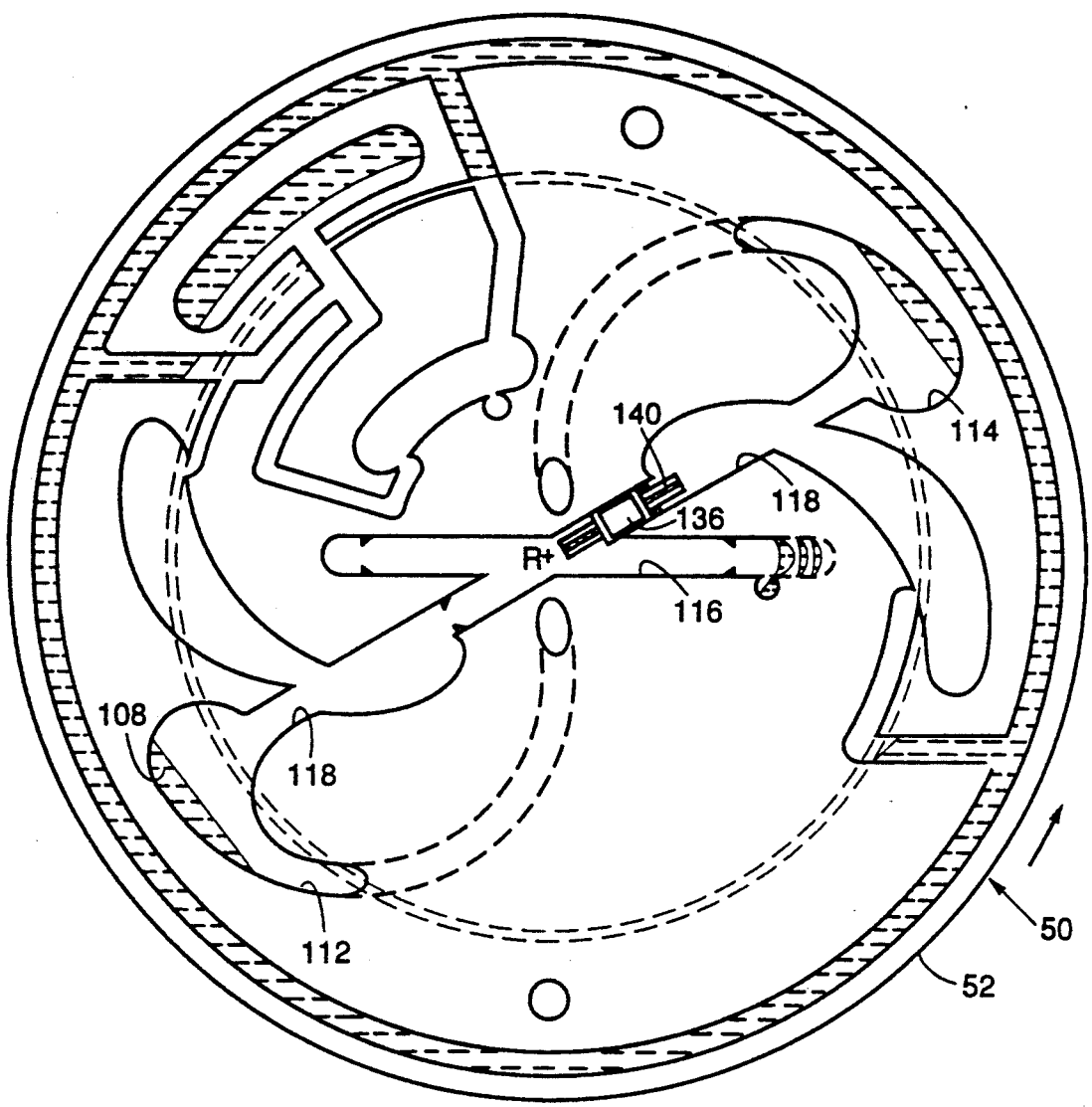
Figure 14:
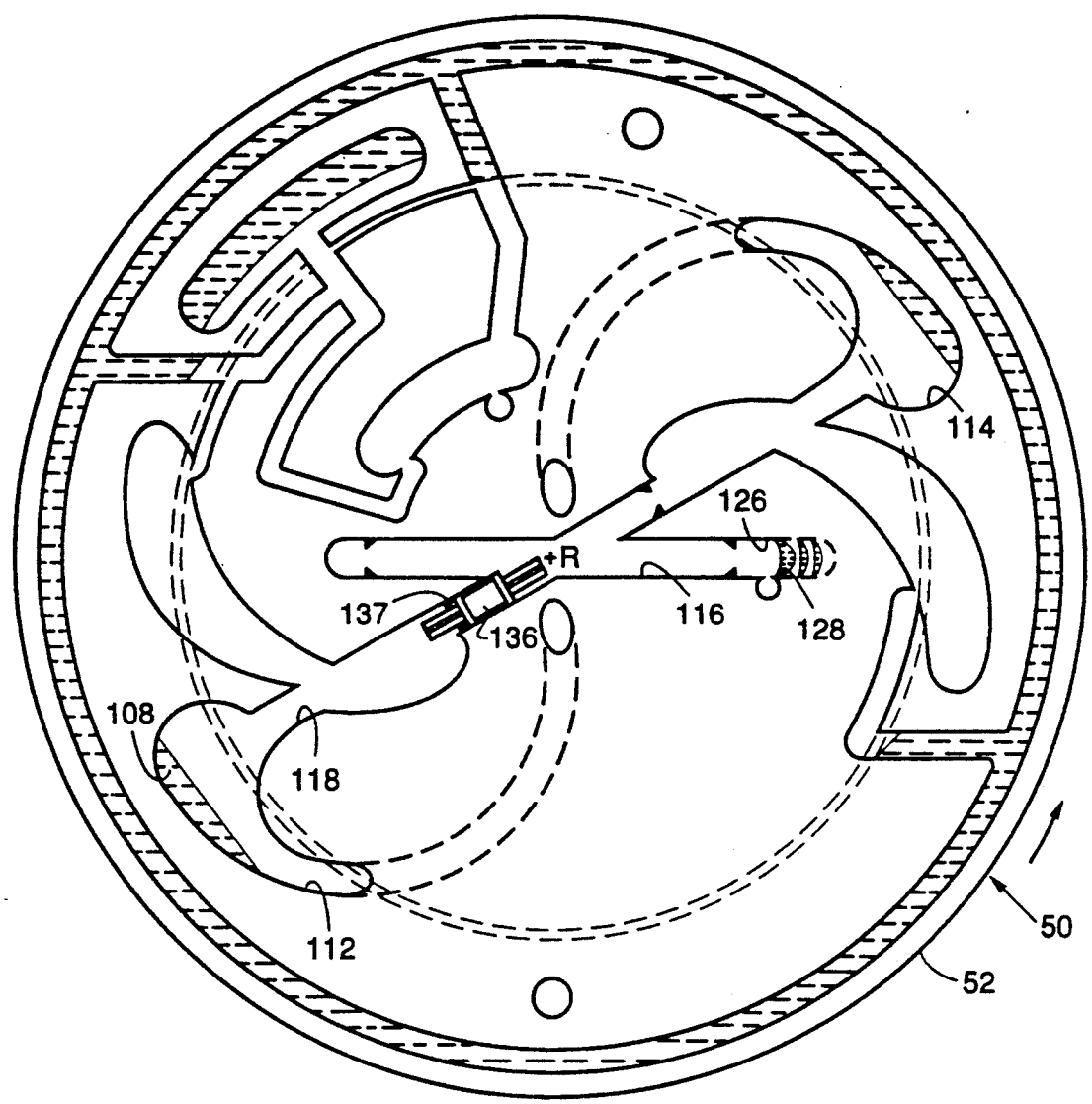

Once filled with supernate, the capillary assembly 136 is moved back across the rotor body 52 and into engagement with the ring 137 as shown in FIG. 13, for discharge of the supernate contents of the tube 40 into the mixing chamber 114. By subsequently spinning the rotor body 52, the supernate collected within the tube 40 is centrifugally expelled therefrom and directed into the chamber 114. The rotor body 52 is then slowly stopped, and the capillary assembly 136 is moved back to the channel reservoir end 126 to obtain another serum sample. The capillary assembly 136, with its serum contents, is then appropriately moved into engagement with the ring 139 positioned within the channel 118. The rotor body 52 is then rotated to expel the serum contents of the tube 40 into the mixing chamber 112, as shown in FIG. 14. The rotor body 52 is then slowly stopped.

Figure 15:
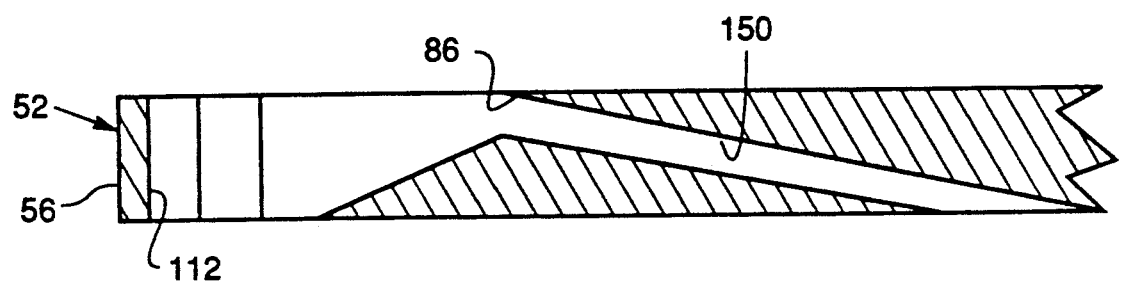
FIG. 15 is a cross-sectional view taken along line 15—15 of FIG. 1.

The mixing chambers 112 and 114 are shaped to facilitate a mixing of the diluent and serum or supernate samples introduced therein and a subsequent transfer of the mixed solution to an external surface of the rotor body 52 for subsequent analysis. To this end, each mixing chamber 112 or 114 is elongated in shape having a bulbous end 146 directed generally clockwise about the rotor body 52, as viewed in FIG. 1, and an exit end 148 directed generally counter-clockwise about the rotor body 52, as viewed in FIG. 1. Each chamber 112 or 114 is disposed relative to the channel 118 so that the channel 118 is joined to the mixing chamber 112 or 114 at a location along the radially-innermost wall thereof intermediate the ends 146, 148. In addition, the exit end 148 communicates with a surface, preferably the bottom surface of the rotor body 52 by means of an arcuate outlet conduit 150 which extends from the exit end 148 to an opening 152 defined along the bottom surface of the body 52 adjacent the rotation axis R. The floors of each mixing chamber 112 or 114, and the conduit 150 are sloped as shown in FIG. 15 for a purpose apparent herein.

Figure 16:
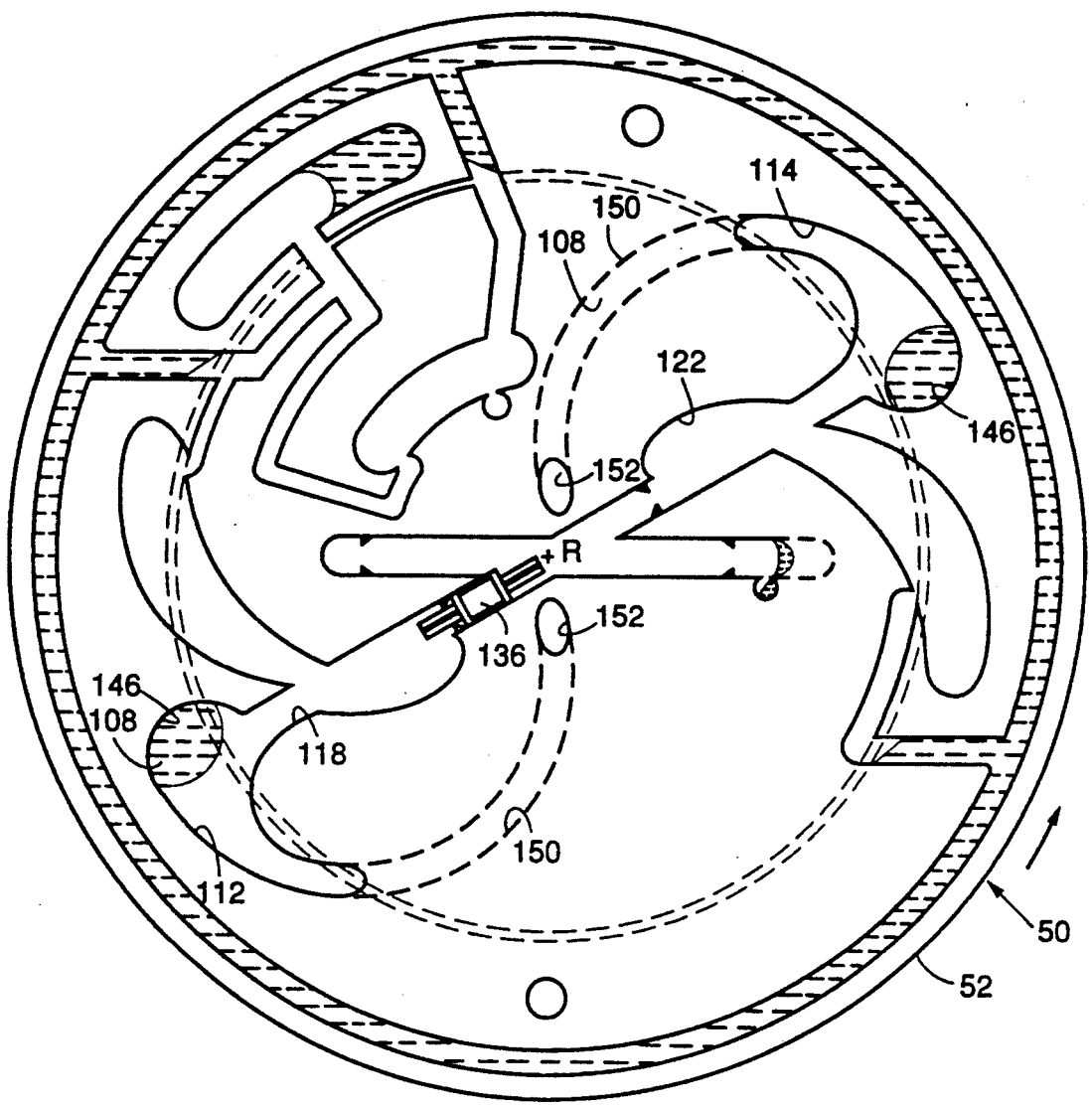
FIGS. 16 and 17 are views similar to that of FIG. 3 illustrating in sequence the various conditions of fluid contents of the rotor body during a mixing step and a subsequent step involving the transference of mixed fluid from the mixing chambers
Figure 17:
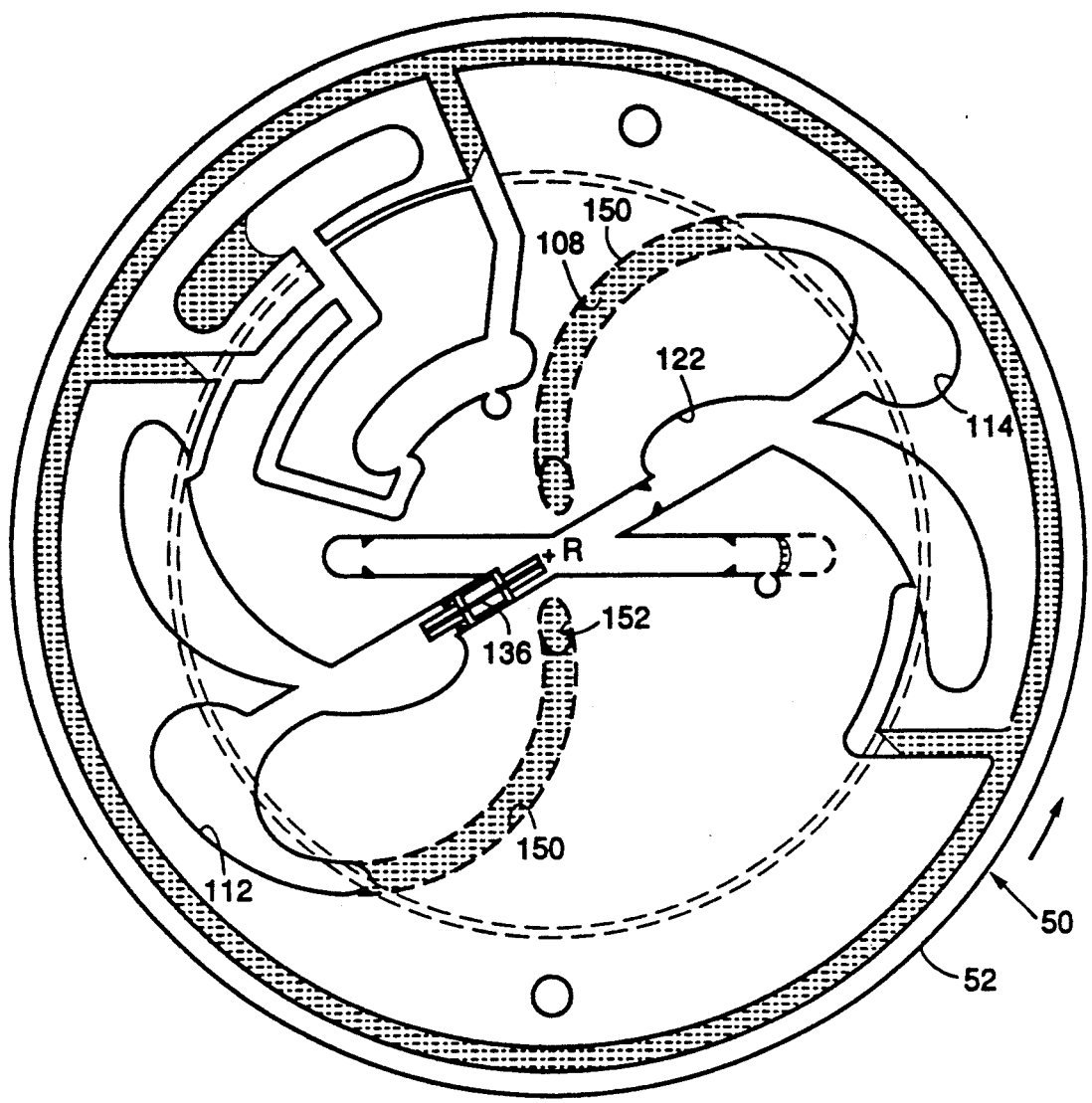

In order to thoroughly mix the contents of the mixing chamber 112 and 114, the rotor is rotated in a clockwise direction about the axis R, as viewed in FIG. 1, and rapidly braked to a stop. The sudden stopping of the body 52 mixes the chamber contents within the chamber end 146 as shown in FIG. 16. In order to subsequently transfer the mixed liquid contents through the outlet conduits 150, the rotor body 52 is rapidly rotated in a counterclockwise direction and braked to an abrupt stop. The momentum imparted to the mixed contents of the mixing chambers 112, 114 during rotation of the rotor body 52 urges the liquid contents through the outlet conduits 150 toward the rotor body openings 152 when the body 52 is suddenly stopped, as shown in FIG. 17. Because the floor of the mixing chambers 112, 114 and conduits 150 are sloped in the manner illustrated in FIG. 15, a premature flow of liquid through the outlet conduits 150 from the chambers 112, 114 is prevented and transference of the liquid from the exit end 148 to the opening 152 is assisted by gravity. In addition, the slope of the conduits 150 prevents undesirable liquid backflow.

Figure 31:
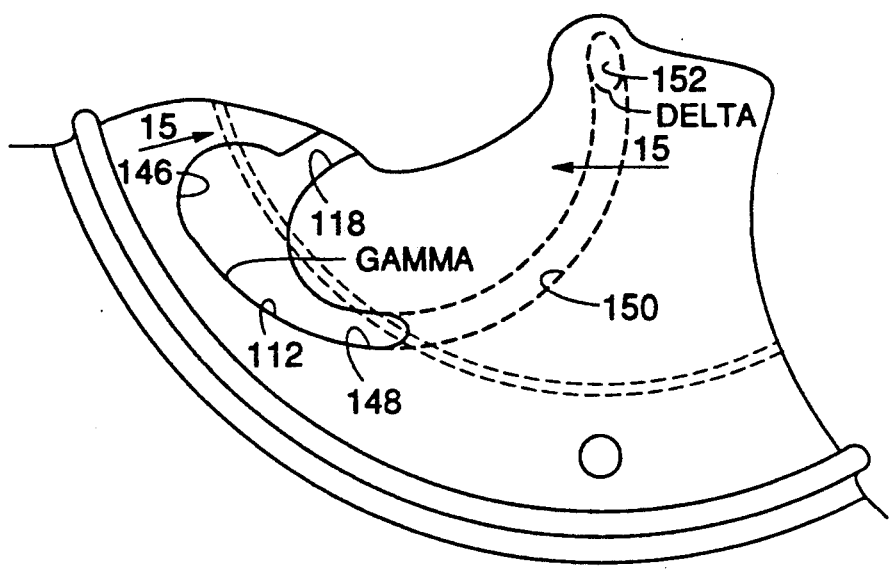
FIG. 31 is a cut-away view of the rotor assembly of FIG. 1 illustrating features related to transference of liquid from one cavity to another.
Figure 32:
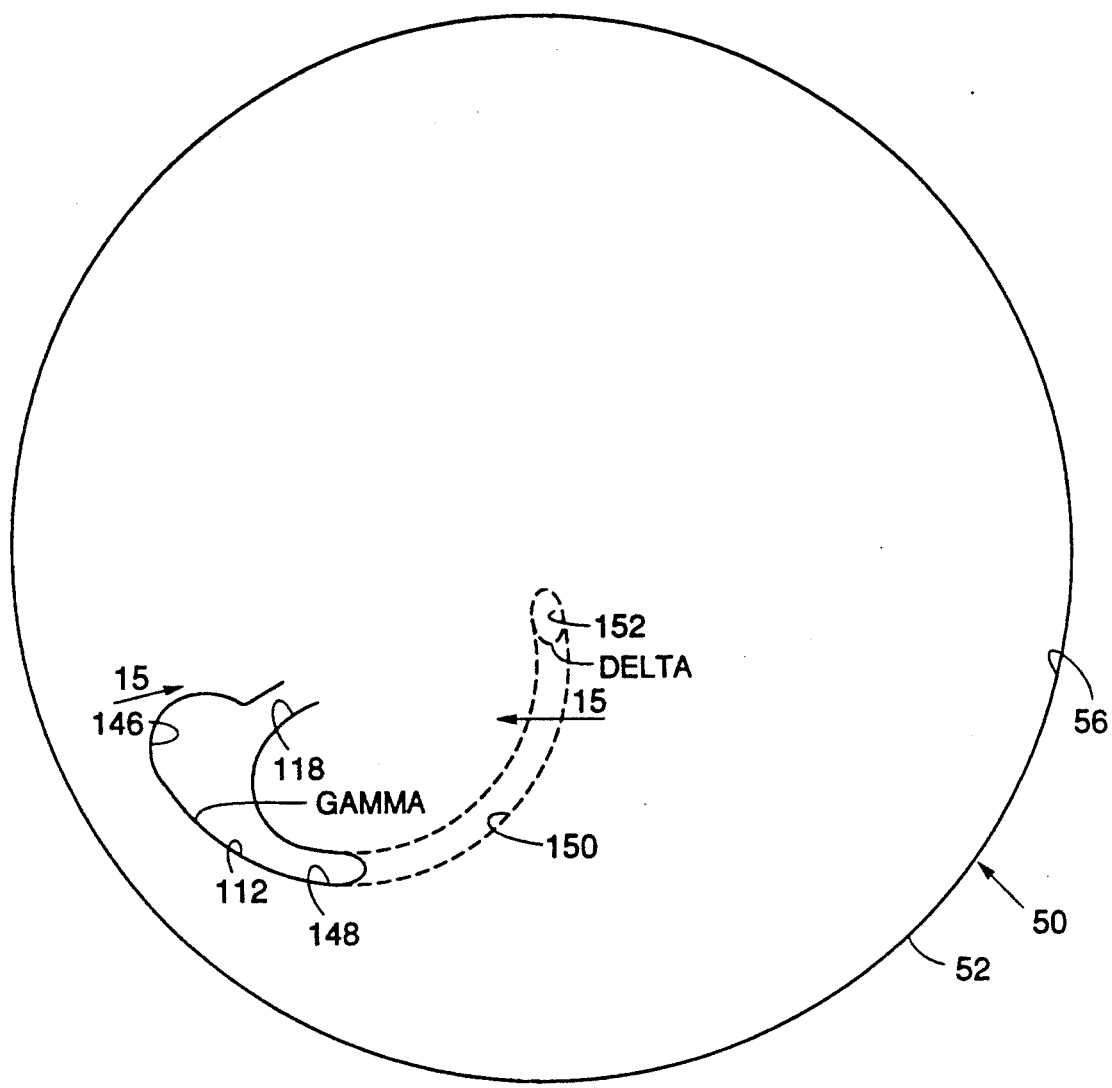
FIG. 32 is a plan view of a stand-alone rotor assembly embodiment similar to the cut-away view shown in FIG. 31.

Once the mixed liquid is transferred through the body openings 152, it enters the filling openings of an underlying analyzer rotor (not shown) for subsequent analysis of the mixed liquid. As an alternative, analysis cuvettes could be made a part of the rotor assembly 50 so that they are filled from the outlet conduits 150. Pertinent views of this particular aspect of the invention are also found in FIGS. 31 and 32.

Figure 18:
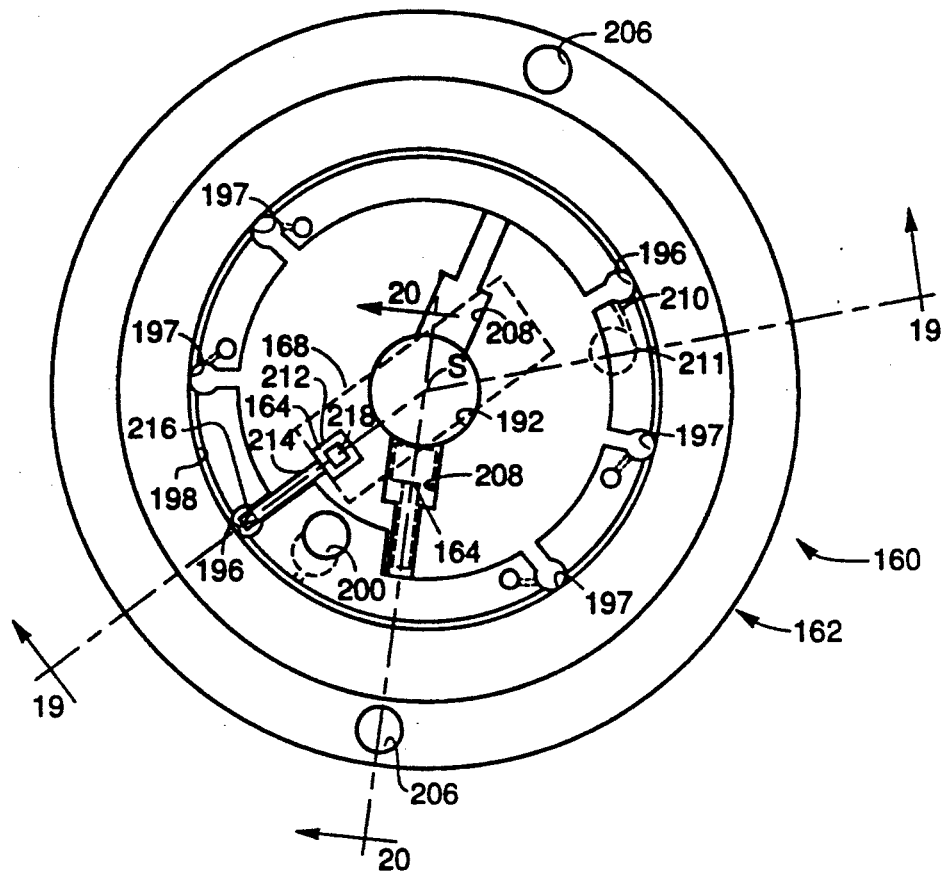
FIG. 18 is a plan view of a rotor body of an alternative assembly embodiment shown with the top plate removed.
Figure 19:
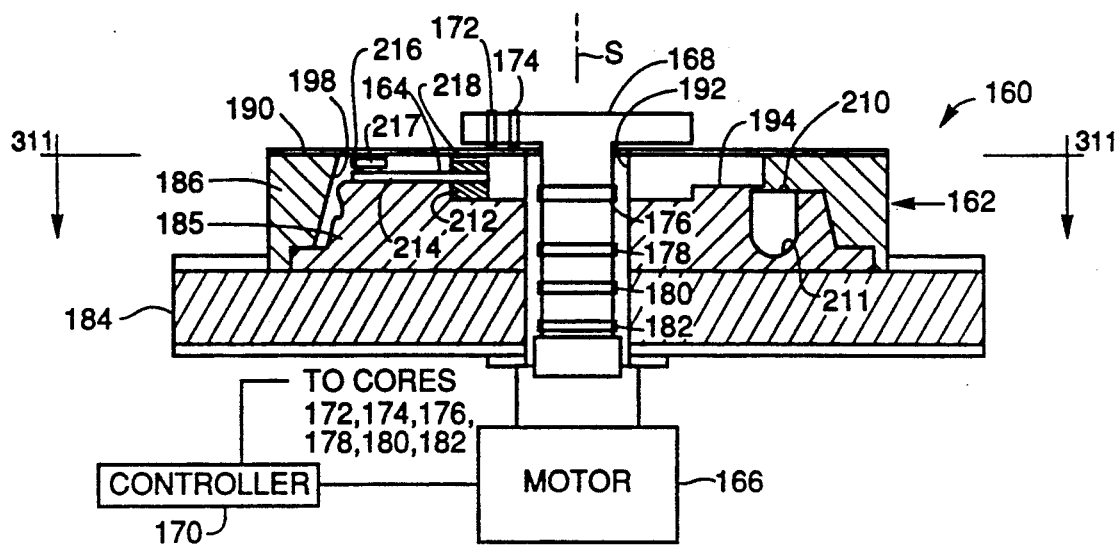
FIG. 19 is a cross-sectional view taken about on line 19—19 of FIG. 18 and illustrating in schematic form components for operating the FIG. 18 rotor body.

With reference to FIGS. 18 and 19, there is illustrated another embodiment, indicated 160, of a rotor assembly in accordance with the present invention. The assembly 160 includes a rotor body 162, a capillary measuring or shuttle assembly 164 positioned within the body 162 and an electric motor 166 for rotating the body 162 about a rotational axis S. The assembly 160 also includes a magnetic assembly mounting member 168 (illustrated in phantom in FIG. 18 for clarity) having a series of electromagnetic cores 172, 174, 176, 178, 180, 182 attached thereto and control means 170 for selectively energizing and de-energizing preselected ones of the cores. As will be described herein, the shuttle assembly 164 is positioned within the body 162 for sliding movement between various locations therein and is moved between such locations by selectively energizing preselected ones of the cores. Therefore and in contrast to the aforedescribed assembly 50 of FIGS. 1–17, the assembly 160 circumvents any need for manual manipulation of a magnet adjacent the capillary measuring assembly 164.

Although the embodiment 160 is shown and described herein as including a series of magnetic cores for moving the shuttle assembly 164 between various locations within the rotor body 162, it will become apparent that movement of the assembly 164 through the body 162 can be effected by a single magnet positioned within the body 162 and movable therethrough in horizontal, vertical or horizontal and vertical directions. Accordingly, the principles of the present invention can be variously applied.

As best shown in FIG. 19, the rotor body 162 includes a lower portion 184, a middle portion 185, an upper portion 186 and a top cover 190 assembled and sealed in the manner illustrated. A central bore 192 extends through the body 162, and the middle and upper portions 186, 188 define a network of passageways and cutouts, described herein, which provide a series of chambers within which processing steps are performed and along which the shuttle assembly 164 can be moved.

Figure 20:
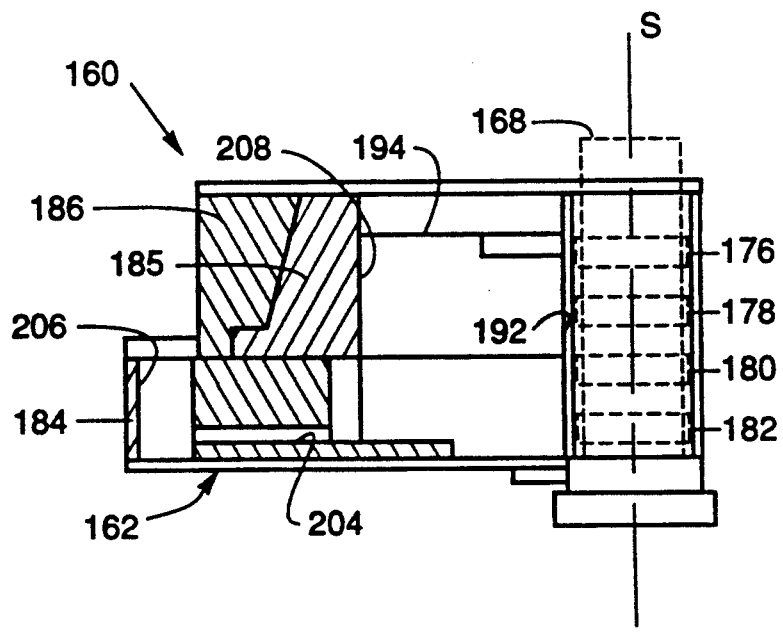
FIG. 20 is a cross-sectional view taken about on line 20—20 of FIG. 18.

More specifically and with reference still to FIGS. 18 and 19, the middle portion 186 defines a cutout section 194 providing a support surface along which the shuttle 164 can be moved horizontally, as viewed in FIG. 19, and a series of discrete compartments in the form of processing chambers 196 and reaction chambers 197 spaced at various intervals around the periphery of the middle portion 186. The upper portion 188 defines a cutout providing a distribution channel 198 extending for a portion of the distance around the periphery of the middle portion 186. An overflow channel 210 and overflow chamber 211 communicates with the distribution channel 198 to prevent an overfilling of the chambers 196 in a manner described herein. A sample, such as a whole blood sample, can be introduced within the body 162 through a septum or access port 200 defined in the cover 190 and which communicates with the distribution channel 198. As shown in FIG. 20, the lower portion 184 defines a radially-extending passageway 204 leading to a circular recess providing a cuvette 206, and the passageway 204 and cutout section 194 communicate with one another through a vertically-oriented slot 208 defined in the middle and lower portions 184, 186. As is explained herein, the slot 208 provides a channel through which the shuttle assembly 164 is moved vertically through the body 162 between the cutout section 194 and the passageway 204.

With reference again to FIG. 18, the shuttle assembly 164 includes a holder body 212 slidably positioned within the cutout section 194 and a straight capillary tube 214 of predetermined length and cross-sectional area which is supported within the holder body 212 so that its longitudinal axis is oriented generally radially of the rotor body 162. In accordance with the present invention, there is incorporated within the holder body 212 of the shuttle assembly 164 a magnetically-attractable material 218 with which the movement of the assembly 164 is guided between various locations within the rotor body 162. In this connection, the holder body 212 includes a major portion which is comprised of a lightweight material, such as an acrylic plastic, and the magnetically-attractable material 218 includes a strip of iron which is glued or otherwise attached atop the major portion of the holder body 212.

As shown in FIG. 19, the magnetic assembly mounting member 168 is generally T-shaped in form and is arranged so that the base leg of its T is positioned within the central bore 192 and the arms of the T are superposed above the top cover 190. The base of the T is coupled to the motor 166 by means of an appropriate coupling arrangement so that the member 168 rotates with the rotor body 162 as the rotor body 162 is rotated about the axis S yet permits independent rotation of the member 168 relative to the body 162 to accommodate an indexing of the angular position of the member 168 relative to the body 162.

The electromagnetic cores 172 and 174 are attached to the member 168 along one arm of its T as shown in FIG. 19 and are positioned therealong so that the core 174 is positioned radially inwardly of the core 172 and both cores 172, 174 are positioned radially inwardly of the outermost position, as shown in FIG. 19, of the shuttle assembly 164. The cores 176, 178, 180 and 182 are attached along the base leg of the member 168, as shown in FIG. 19, and are positioned in a sequential fashion along the length of the slot 208 (FIG. 20) so that the lowermost core 182 is positioned at about the vertical level of the radial passageway 204.

Figure 21:
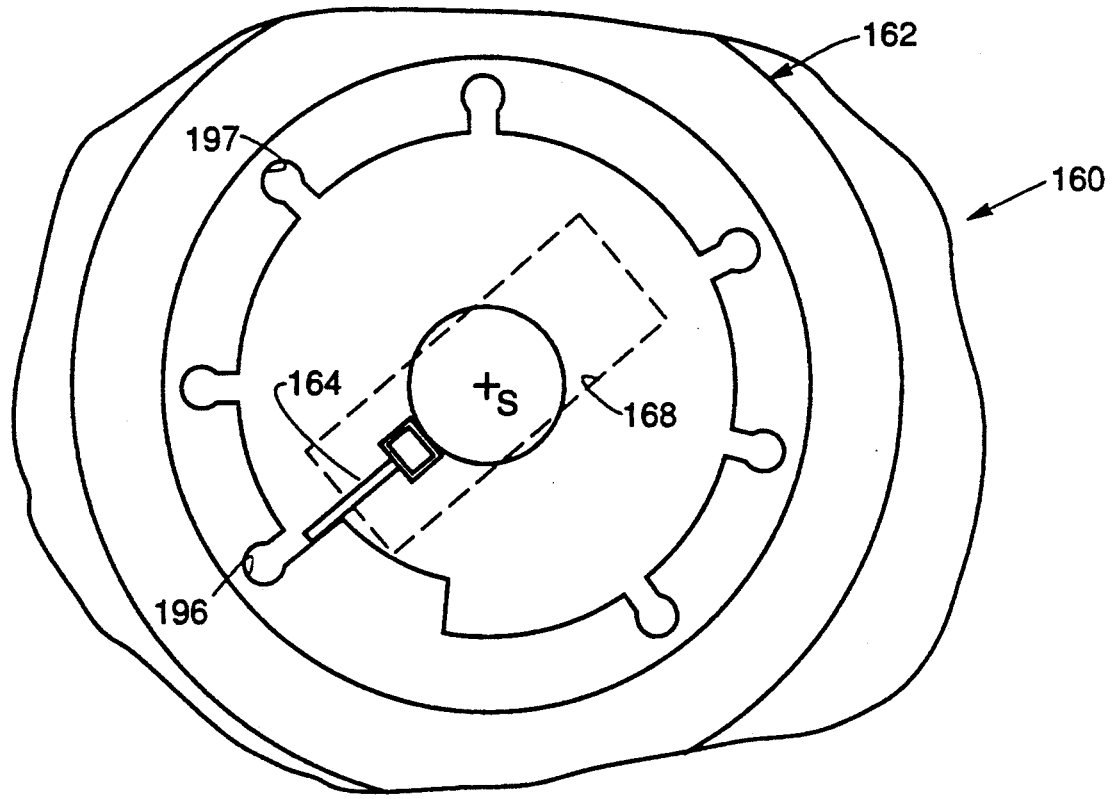
FIGS. 21–23 are fragmentary cross-sectional views taken about on line X—X of FIG. 19 illustrating sequential positions of the capillary measuring assembly of the rotor assembly when moved between discrete chambers of the rotor body.
Figure 22:
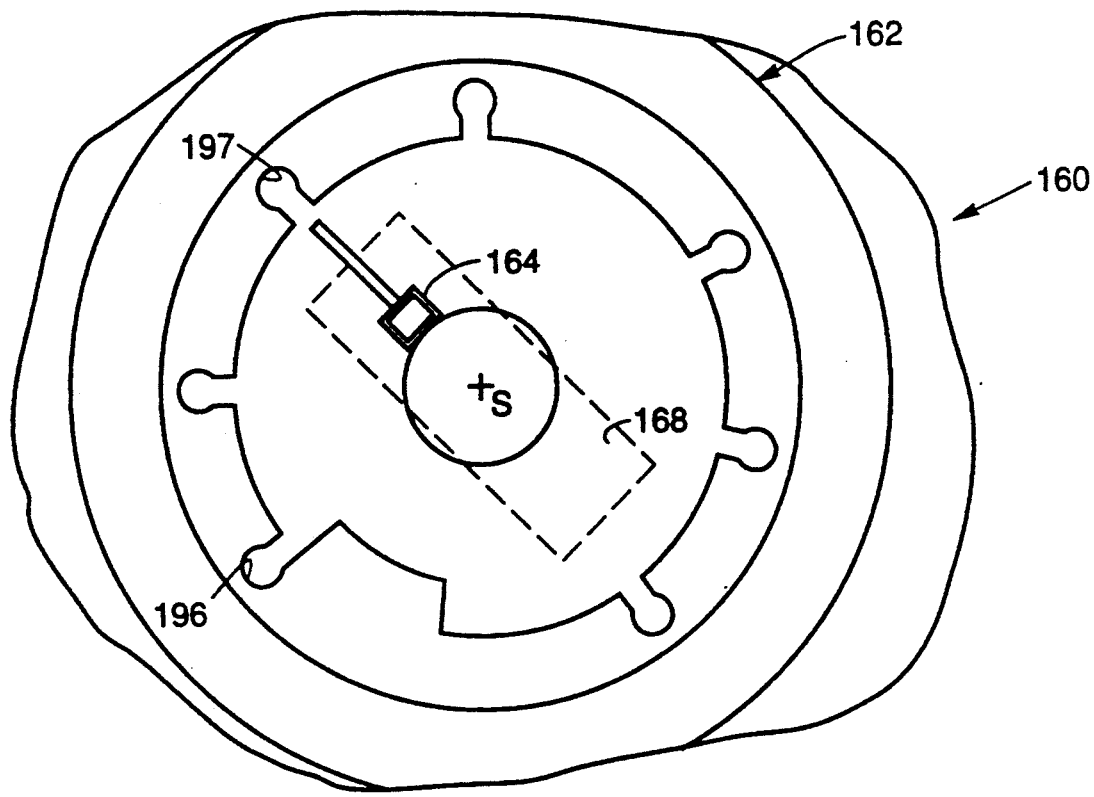

In order to move the shuttle assembly 164 from a processing chamber 196 to a reaction chamber 197, the rotation of the rotor body 162 is stopped and the magnetic assembly mounting member 168 is rotated to a position at which the core-supporting arm of the member 168 is positioned along a radial path which corresponds to the direction in which the capillary tube 214 of the shuttle assembly 164 is directed, as shown in FIG. 18. The core 172 is then energized so that the holder body 212 of the shuttle assembly 164 is magnetically moved radially inwardly from its FIG. 18 position to a second position at which the assembly holder body 212 is positioned directly beneath the core 172. The core 174 is then energized and the core 172 is de-energized so that the shuttle assembly 164 is magnetically moved radially inwardly to a third position, as shown in FIG. 21, at which the holder body 212 is positioned directly beneath the core 174. In this third position, the capillary tube 214 is completely extracted from the chamber 196. The member 168 is then manually or automatically indexed relative to the rotor body 162 so that the core-bearing arm of the member 168 is directed along a radial path oriented generally toward a reaction chamber 197, as shown in FIG. 22. The magnetic attraction between the core 174 and holder body 212 maintains the holder body 212 directly beneath the core 174 while the member 168 is indexed so that the shuttle assembly 164 is forced to move with the member 168 to the FIG. 22 position at which the longitudinal axis of the capillary tube 214 is directed generally toward the chamber 197.

Figure 23:
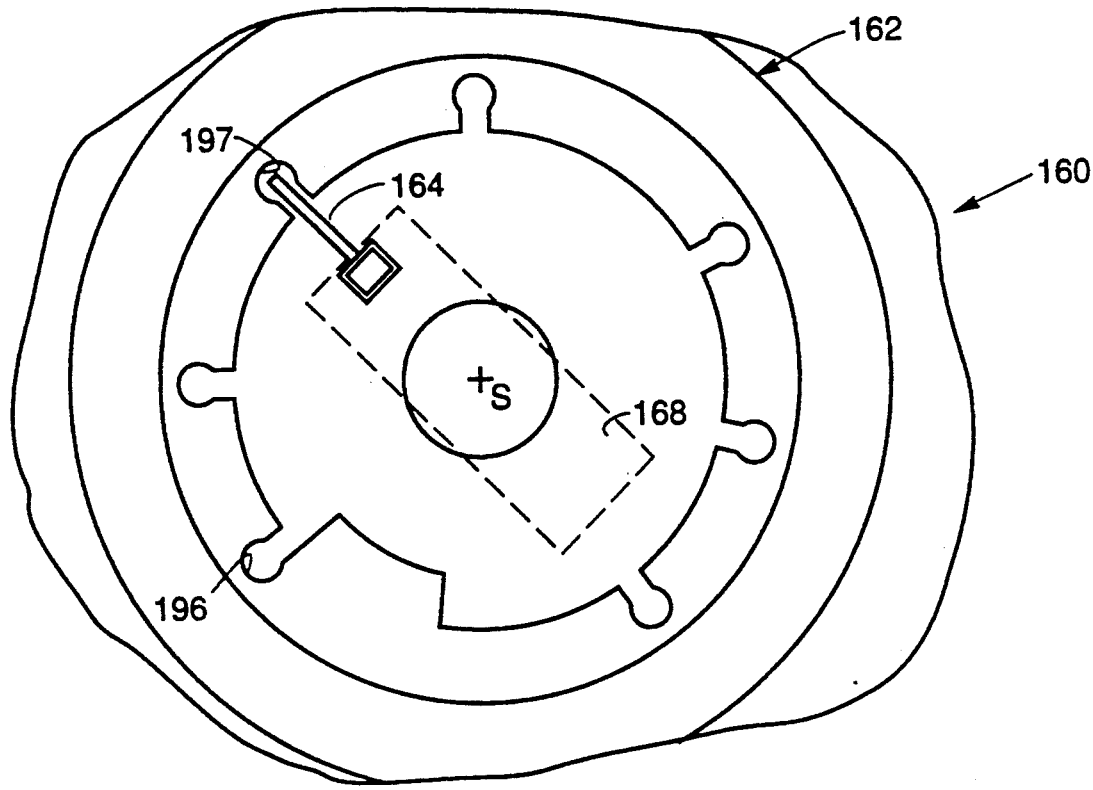

The electromagnetic core 174 is then de-energized and the rotor body 162 is rotated so that the centrifugal forces generated from the rotation of the body 162 shifts the shuttle assembly 164 radially outwardly into operative position within the reaction chamber 197, as shown in FIG. 23.

Figure 24:
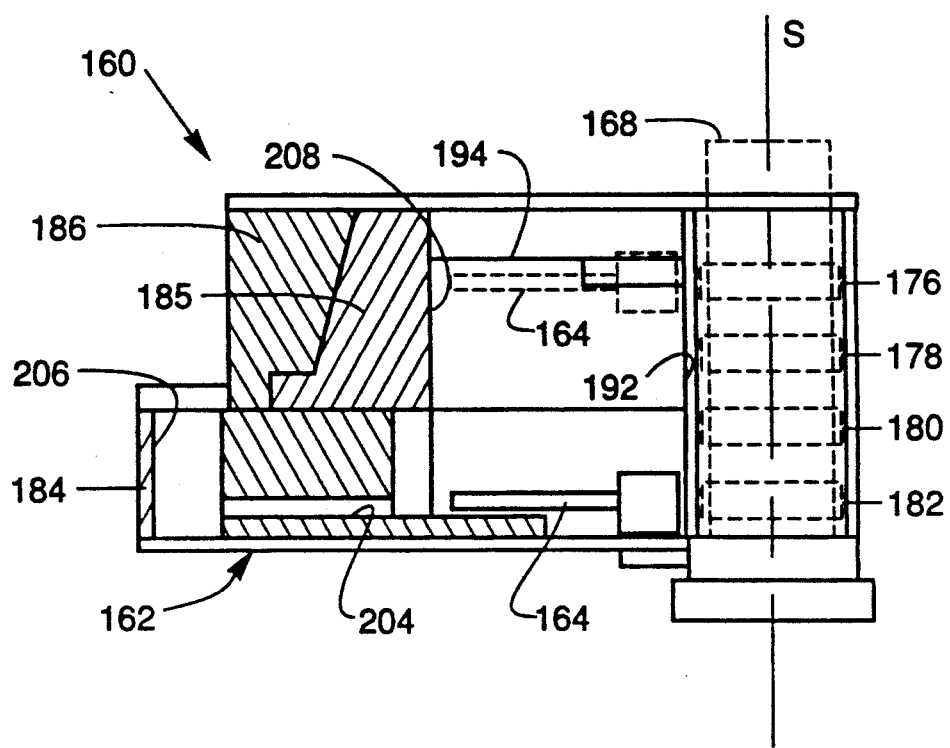
FIG. 24 is a view similar to that of FIG. 20 illustrating sequential positions of the capillary measuring assembly when moved vertically through the rotor body.

In order to move the shuttle assembly 164 from the cutout section 194 to the vertical level of the radial passageway 204 defined in the lower portion 184, the cores 172, 174 are appropriately energized and/or de-energized in the manner described above so that the holder body 212 is positioned directly beneath the core 174, as shown in FIG. 21. The member 168 is then indexed counterclockwise, as viewed in FIG. 18, relative to the rotor body 162 so that the shuttle assembly 164 is arranged in the position illustrated in phantom in FIG. 18 at which the shuttle assembly 164 is positioned in registry with the appropriate slot 208. The core 176 (FIG. 24) is then energized, and the core 174 is de-energized to magnetically move the assembly 164 downwardly to the position illustrated in phantom in FIG. 24, which position corresponds to the vertical level of the core 176. At that point, the core 178 is energized and the core 176 is de-energized so that the assembly 164 is moved downwardly to the vertical level of the energized core 178. In a similar manner, cores 180 and 182 are sequentially energized and cores 178 and 180 are de-energized to ultimately position the shuttle assembly 164 at about the vertical level of the core 182 and thus the vertical level of the radial passageway 204. The core 182 is subsequently de-energized and the rotor body 162 is rotated to centrifugally shift the shuttle assembly 164 radially outwardly into operative position within the passageway 204.

For illustrative purposes and to illustrate the operation of the rotor assembly 160, a whole blood sample is initially introduced into the rotor body 162 through the access port 200, and then the rotor body 162 is rotated so that the sample travels through the distribution channel 198 to fill the processing chambers 196 up to the radial level of the overflow channel 210. The blood sample is subjected to centrifugal forces during such rotation so that the blood plasma separates from the cellular components of the blood. Upon halting the rotation of the body 162, an aliquot of plasma is drawn into the capillary tube 214 of the shuttle assembly 164 by capillary action from a chamber 196 for transfer to a reaction chamber 197 for subsequent processing as desired. The reaction chamber 197 could, for example, contain reagents, or reagents could be introduced into another discrete chamber for subsequent transference to a reaction chamber 197 through an appropriate channel.

For tests that require the use of a solid phase reaction pad 217 (FIG. 19), such a pad could be operatively attached by suitable means 216 to the shuttle assembly 164 for deposit within the desired discrete chamber. Once the reaction pad 217 is positioned in radial registry with the desired chamber, the assembly 164 and the reaction pad 217 supported thereby is moved into operative position within the chamber by de-energizing any cores carried by the member 168 and rapidly rotating the body 162. Depending upon the test being performed, the reaction pad 217 could be withdrawn from one reaction chamber by the shuttle assembly 164 and directed into another reaction chamber for subsequent reactions. It follows that by energizing and de-energizing the electromagnetic cores 172, 174, 176, 178, 180 and 182 in the aforedescribed manner, the shuttle assembly 164 can be moved into and out of discrete chambers of the rotor body 162, which chambers are located vertically and/or horizontally in relation to one another.

Once the various aliquots of liquids have been processed within the rotor assembly 160 through the various steps required by a given analytical process, an aliquot of the resultant preparation is mixed with an aliquot of reagent within the cuvettes 206. The resultant mixture is optically monitored using a conventional centrifugal analyzer. By combining the processing steps and the monitoring steps in one integrated component, the entire analytical process can be automatically performed in a sealed system.

The aforedescribed rotor assembly 160 is advantageous in that it combines the principles of capillary action, centrifugal force and magnetic force to process, transfer, mix and monitor liquids in compartments located in three-dimensional space. In addition, reaction substances and samples can be transported between processing compartments with the use of capillary action, centrifugal force or magnetic force. Furthermore and as mentioned earlier, the control means 170 (FIG. 18) is operatively connected to the electromagnetic cores and the motor 166 for automatically controlling the energizing and de-energizing of the cores and the rotation of the rotor body 162. Therefore, due to the capacity of the rotor assembly 160 to confine processing steps internally of the rotor body 162 and limit the need for manual intervention of an analyst, analysis methods carried out with the assembly 160 are likely to provide accurate results and reduce the exposure of an analyst to potentially harmful substances being analyzed.

Figure 25:
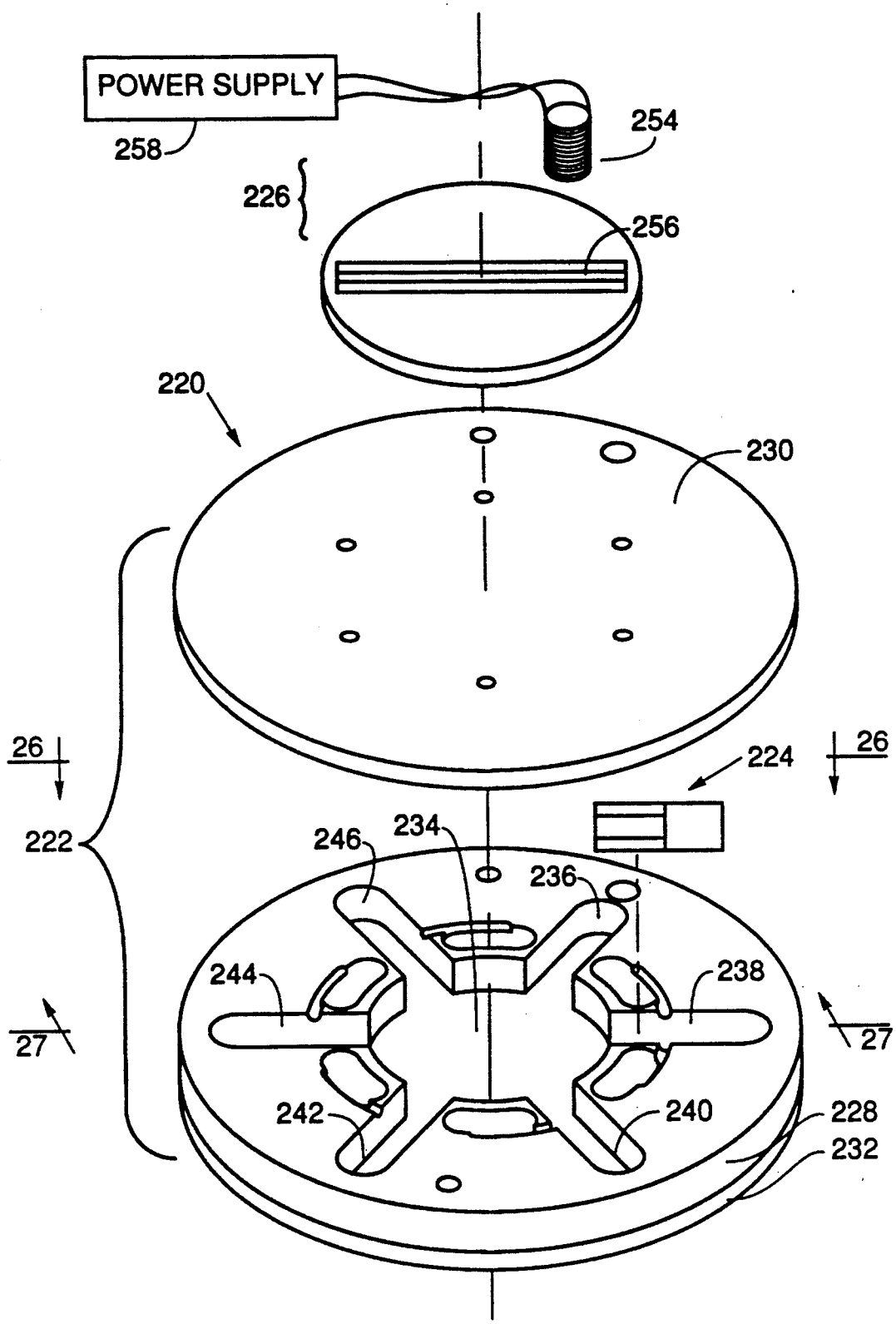
FIG. 25 is a perspective view of a rotor body of another alternative assembly embodiment, shown exploded.
Figure 26:
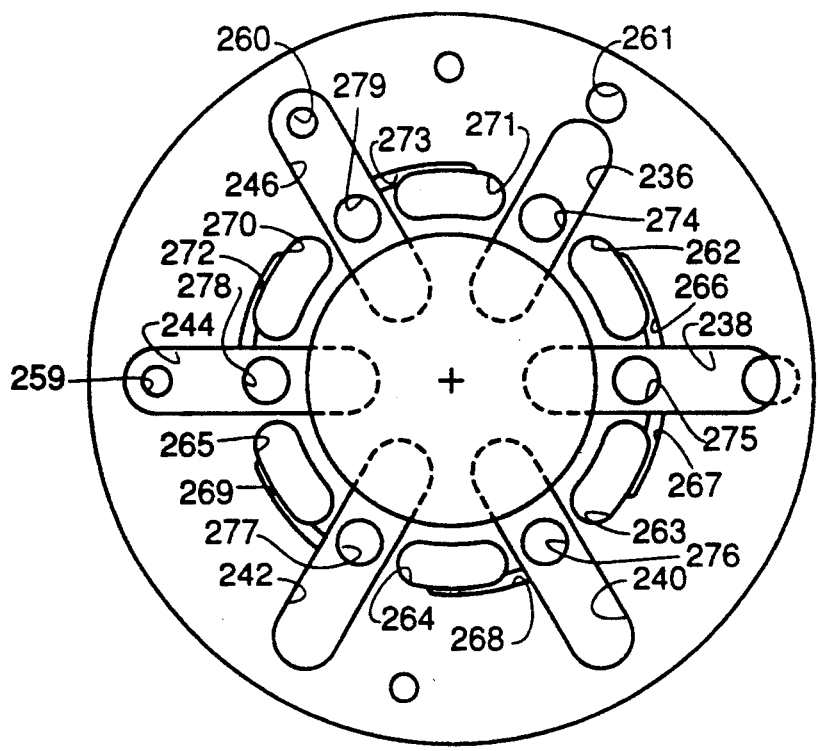
FIG. 26 is a plan view of the rotor body as viewed along line 26—26 of FIG. 25.
Figure 27:
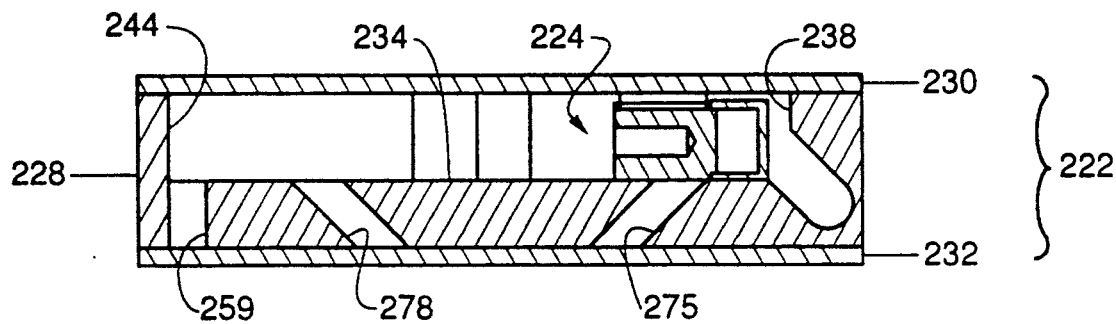
FIG. 27 is a cross section taken along line 27—27 of FIG. 25 illustrating the shuttle when positioned in operative registry with one of the rotor body chambers.

With reference to FIGS. 25-27, there is illustrated still another embodiment, rotor assembly 220, of a rotor assembly which has been found to be well-suited for use in an enzyme-linked immunosorbent assay (ELISA). The rotor assembly 220 includes a rotor body 222, a shuttle assembly 224 containing either a reaction vessel, a solid phase reaction pad support means, or a capillary assembly, and a magnet assembly 226. In addition, the rotor assembly 220 is designed to operate with a conventional centrifugal analyzer that can be used to generate centrifugal force and to monitor and process reactions within the body 222.

The rotor body 222 is comprised of a central body 228 and top and bottom cover windows 230 and 232, respectively. The central body 228, fabricated from a disk, having a diameter of 8.8 cm, cut from a sheet of opaque plastic, contains various compartments including a central circular chamber, or switching yard, 234 and six separate chambers 236, 238, 240, 242, 244, 246 that are connected to and radiate from the central chamber 234. During operation of the rotor assembly 220, these radiating chambers operate as separate liquid processing units. Two of the chambers 244, 246 have circular holes 259, 260 drilled through them and, with the addition of the cover windows 230, 232, serve as cuvettes for optical monitoring of the liquid contents of the two of the chambers 244, 246. A third hole 261 acts as an air-filled reference for the centrifugal analyzer optical monitoring system. Five of the six separate chambers have ancillary receiving chambers 262, 263, 264, 265, 270, 271 and associated connecting channels 266, 267, 268, 269, 272, 273 through which aliquots of liquids are introduced to the corresponding chambers 238, 240, 242, 244, 246. The base of each chamber 236, 238, 240, 242, 244, 246 contains a sloped cavity 274, 275, 276, 277, 278, 279 slope in the manner exemplified by chambers 275 and 278 of chambers 238 and 244, respectively, shown in FIG. 27. During operation of the assembly 220, these sloped cavities prevent cross transfer of any liquids between chambers when the rotor is not rotating and the liquids are not being held toward the outer edges of the chamber by centrifugal force.

The top cover window 230 is fabricated from a disk of ultraviolet-transmitting material and six apertures are machined therein to provide access to the liquid-receiving chambers in the rotor body 222. The central body 228 and top and bottom windows 230, 232 are assembled and sealed into a single body 222 by suitable means. The rotor body 222 is envisioned as a disposable unit for disposal after one use, and to this end can be constructed relatively inexpensively.

Figure 28:
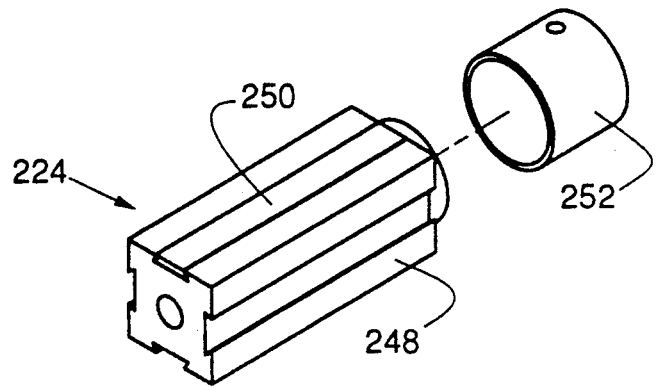
FIG. 28 is an exploded perspective view of the shuttle of the FIG. 25 assembly embodiment.

For purposes of moving a reactive surface containing an immobilized antibody or antigen into and out of the chambers 236, 238, 240, 242, 244, 246 of the rotor body 222, the shuttle 224 is positioned within so as to slidably move along the compartments of the rotor body 222. As shown in FIG. 28, the shuttle 224 includes a major portion 248 which has been machined from a block of acrylic plastic and includes a strip 250 of magnetically-attractable iron glued into a channel which has been appropriately machined into the top surface of the major portion 248 and which provides the shuttle 224 with a magnetic handle. To enable the shuttle 224 to transport reaction vessels or solid phase reaction pads from one location in the body 222 to another body location, a small reaction cup 252 is attachable to one end of the shuttle 224, and small holes are drilled into the cup 252 to provide liquid access to the internal walls thereof when the cup 252 is inserted into a processing chamber 236, 238, 240, 242, 244 or 246 of the rotor body 222. The cup 252 is of such size and shape so as to be attached to the shuttle 224 as the cup 252 cooperatively mates with a cylindrical lip that has been machined onto the end of the shuttle 224.

As an alternative to the reaction cup 252, the shuttle 224 may include a measuring capillary, like that of the measuring capillary 164 of the rotor assembly 160 of FIGS. 18–21. With a measuring capillary incorporated therein, the shuttle 224 can be used to sample, transport, and deliver measured aliquots from and into designated chambers within the rotor body 222 with the use of capillary action and magnetic and centrifugal forces.

With reference again to FIG. 25, the magnet assembly 226 includes a electromagnet 254 which has been mounted on a horizontal track 256 located above the rotor body 222. Voltage and current is supplied to the electromagnet 254 by means of a variable power supply 258. Positioning of the magnetic field relative to the rotor body 222 and the shuttle 224 is accomplished by moving the magnet 254 back and forth on the track 256. As an alternative to the magnet assembly 226, a small permanent magnet can be used to move and position the shuttle 224 within the rotor body 222.

In order to move the reaction cup 252 between the separate chambers 236, 238, 240, 242, 244, 246, the shuttle 224 is initially moved into or positioned into the central chamber 234 of the rotor body 222. The magnet 254 is then positioned over the shuttle 224 and its magnetic strip 250 and appropriately manipulated so that by orienting and positioning the magnetic field of the magnet 254 relative to the rotor body 222, the reaction cup 252 can be positioned into a desired one of the processing chambers 236, 238, 240, 242, 244, 246. To remove the reaction cup 252 from the desired chamber, the centrifugal field is removed by halting the rotation of the body 222, and the magnet 254 is again placed over the iron strip 250 of the shuttle 224. By moving the magnet 254 and its magnetic field inwardly toward the center of the rotor body 222, the shuttle 224 is moved back into the central chamber 234. The shuttle 224 can then be positioned in front of a different processing chamber by appropriately rotating and indexing the rotor body 222 relative to the position of the magnet 254 for subsequent insertion into the different chamber. The aforedescribed series of steps including moving, indexing and positioning and the times required to perform each step can be programmed into a suitable controller for automatically completing a series of specific analytical operations.

As mentioned earlier, the assembly 220 has been found to be useful for performing an ELISA procedure. For performing an exemplary ELISA procedure whose steps are outlined below, one processing chamber 238 is dedicated to blood processing, one processing chamber 240 is dedicated to washing, one processing chamber 242 is dedicated to conjugate addition, another processing chamber 244 is dedicated to reagent monitoring, another processing chamber 236 is dedicated to drying, and the remaining processing chamber 246 is dedicated to substrate addition and subsequent reaction monitoring. In addition, an immobilized antigen or antibody is introduced into the reaction cup 252. With the aforesaid dedication of processing chambers, the following procedural steps are sequentially performed:

A. Introduction of 700 $\mu$l of a whole blood sample into chamber 238 through receiving chambers 262 and 263.

B. Rotating rotor body 222 at 4000 rpm for five minutes to centrifugally separate the whole blood into cellular and plasma levels.

C. Inserting the reaction cup 252 into chamber 238 and into operative engagement with the plasma layer while the rotor body 222 is being rotated at about 500 rpm to thereby initiate binding between the immobilized antigen or antibody contained within the reaction cup 252 with the soluble antigen or antibody contained within the sample.

D. Incubate reaction cup 252 in the plasma layer for two minutes while the rotor body 222 continues to rotate.

E. Stop the rotation of the rotor body 222 and remove reaction cup 252 from chamber 238.

F. Index and position the reaction cup 252 into chamber 240 which contains approximately 250 $\mu$l of wash solution.

G. Wash as necessary by rotating the rotor body 222 at about 500 rpm with the reaction cup 252 immersed in the wash solution for several seconds, stopping the rotation of the rotor body 222, removing the reaction cup 252 from the chamber 240, placing the reaction cup 252 into the drying chamber 236, rotating the rotor body 222 for several minutes at 4000 rpm to remove the remaining liquid from the reaction cup 252, and then stopping the rotor body 222 for the next step.

H. Remove reaction cup 252 from drying chamber 236 and index and position it in front of chamber 242 which contains 250 $\mu$l of enzyme conjugate.

I. Insert reaction cup 252 into chamber 242 to thereby initiate binding of enzyme conjugate with bound antigen/antibody complex.

J. Incubate reaction cup 252 in the enzymeconjugate for two minutes while rotating rotor body 222 at about 500 rpm.

K. Remove reaction cup 252 from chamber 242 and index and position the shuttle 224 into chamber 240 which contains approximately 250 μl of wash solution.

L. Wash a necessary by insertion and removal of reaction cup 252 into and out of wash solution contained within chamber 240 and by events described in step "G" above.

M. Remove reaction cup 252 from chamber 236 and index and position the reaction cup 252 in front of chamber 246 which contains 250 μl of enzyme substrate solution.

N. Insert the reaction cup 252 into the substrate solution of chamber 246 for five minutes while rotating rotor body 222 at about 500 rpm which results in the generation of product from the enzyme conjugate action on the enzyme substrate.

O. Remove the reaction cup 252 from the chamber 246 and place the reaction cup 252 out of the way in the drying chamber 236.

P. The rotor body 222 is then rotated at about 1000 rpm and the reaction is monitored at 405 nm through the cuvette 260 with the use of the optical system of a centrifugal analyzer. The reagent blank chamber 244 would contain a reagent mixture identical to that contained in the reaction chamber 246 except that no product would have been generated since the reaction cup 252 was not placed into the reagent blank chamber 244. The reagent reference would be monitored by the optical system through cuvette 259. The air cuvette 261 sets the maximum transmission for the analyzer optical system.

The aforedescribed ELISA procedure can be performed with in a short period of time with very little human intervention and the rotor body 222 is advantageous in this respect. By similar techniques, a shuttle within which a measuring capillary tube is incorporated can be used to sample, transport and deliver measured volumes of liquid from and into designated chambers of the rotor body 222. By appropriate shuttle design, volumes ranging form 1.0 μl to 750 μl can be transferred between designated chambers by means of the shuttle.

It will be understood that numerous modifications and substitutions can be had to the aforedescribed embodiments without departing from the spirit of the invention. For example, although the rotor body 52 of the rotor assembly 50 of FIGS. 1-17 has been shown and described as including two sets of chambers within which a diluent is separated into measured amounts and subsequently mixed with a sample, a rotor body in accordance with the broader aspects of the invention may include any of a number of such sets of chambers. Accordingly, the aforedescribed embodiments are intended for the purpose of illustration and not as limitation.

What is claimed is:

1. A method for carrying out an assay comprising the step of:
providing a rotor assembly comprising a rotor body which is rotatable about an axis of rotation, said rotor body comprising a central chamber and first, second, third, fourth, fifth, and sixth chambers which are in communication with and radiate from said central chamber, said rotor assembly further comprising a shuttle which is movable through said central chamber and insertable into any of said chambers, said shuttle comprising a reaction cup carrying an immobilized antigen or an immobilized antibody for transport among said chambers;

introducing an amount of whole blood into said first chamber;

introducing a wash solution into said second chamber;

dedicating said third chamber to drying purposes;

introducing an enzyme conjugate into said fourth chamber, said enzyme conjugate being chemically combinable with said immobilized antigen or immobilized antibody;

introducing an enzyme substrate solution into said fifth chamber;

introducing a reagent reference into said sixth chamber, said reagent reference being identical to said enzyme substrate solution;

rotating said rotor body to centrifugally separate said whole blood sample into cellular and plasma components;

stopping the rotation of said rotor body;

inserting said reaction cup into said first chamber to bind one of said immobilized antigen or antibody carried by said reaction cup with soluble antigen or antibody contained within said plasma component to form an antigen/antibody complex;

moving said reaction cup from said first chamber through said central chamber and into said second chamber;

washing said reaction cup by rotating said rotor body with said reaction cup immersed in said wash solution contained within said second chamber, stopping rotation of said rotor body, moving said reaction cup from said second chamber through said central chamber into said third chamber, rotating said rotor body to dry said sample and then stopping the rotation of said rotor body;

moving said reaction cup from said third chamber through said central chamber and into said fourth chamber to bind said enzyme conjugate contained within said fourth chamber with said antigen/antibody complex;

moving said reaction cup from said fourth chamber through said central chamber and into second chamber;

washing said reaction cup by rotating said rotor body with said reaction cup immersed in said wash solution contained within said second chamber, moving said reaction cup from said second chamber through said central chamber and into said third chamber, rotating said rotor body for drying said sample; and then stopping the rotation of said rotor body;

moving said reaction cup from said third chamber through said central chamber and into said fifth chamber and into said substrate solution contained within said fifth chamber to generate a product for analysis;

removing said reaction cup from said fifth chamber; and optically monitoring said product generated in said fifth chamber while rotating said rotor body and comparing said monitor product with said reagent reference contained within said sixth chamber.

2. The method as defined in claim 1 wherein said step of moving said reaction cup from said first chamber is preceded by a step of incubating said reaction cup within said plasma component for a preselected period of time.

3. The method as defined in claim 1 wherein said step of moving said reaction cup from said fourth chamber is preceded by a step of incubating said reaction cup within said enzyme conjugate for a preselected period of time.

4. The method as defined in claim 1 wherein said shuttle includes a magnetically-attractable portion and said steps of moving include steps of generating a magnetic field adjacent said shuttle and moving said magnetic field so that said shuttle is moved by said magnetic field.

5. The method as defined in claim 1 wherein said rotor assembly further comprises a rotating means for rotating said rotor, a moving means for moving said shuttle, and a controller means for automatically controlling at least one of said rotating, stopping, and moving steps.

6. The method as defined in claim 1 wherein said reaction cup comprises a solid phase reaction pad.

* * * * *